United States Patent [19]
Ohta et al.

[11] Patent Number: 5,912,156
[45] Date of Patent: Jun. 15, 1999

[54] POLYPEPTIDE HAVING COLD-STABLE PYRUVATE, ORTHOPHOSHATE DIKINASE ACTIVITY, DNA ENCODING THE SAME AND RECOMBINANT VECTOR AND TRANSFORMED PLANTS CONTAINING THE DNA

[75] Inventors: Shozo Ohta; Satoru Usami, both of Shizuoka, Japan; James Nigel Burnell, Townsville, Australia

[73] Assignee: Japan Tobacco Inc., Tokyo, Japan

[21] Appl. No.: 08/500,857

[22] PCT Filed: Dec. 1, 1994

[86] PCT No.: PCT/JP94/02022

§ 371 Date: Aug. 2, 1995

§ 102(e) Date: Aug. 2, 1995

[87] PCT Pub. No.: WO95/15385

PCT Pub. Date: Jun. 8, 1995

[30] Foreign Application Priority Data

Dec. 3, 1993 [AU] Australia ............................. 52275/93
Jul. 29, 1994 [JP] Japan ................................ 6-197780

[51] Int. Cl.$^6$ ..................... C07H 21/04; C12N 15/00; C12N 9/12; C12N 5/00
[52] U.S. Cl. ................... 435/194; 435/320.1; 435/410; 536/23.2; 935/22
[58] Field of Search .................. 435/194, 320.1, 435/410, 240.4; 536/23.2; 935/22

[56] References Cited

FOREIGN PATENT DOCUMENTS

| WO95/09234 | 4/1995 | WIPO . |
| 95/15385 | 6/1995 | WIPO ................... 435/194 |
| 96/04369 | 2/1996 | WIPO ................... 435/194 |

OTHER PUBLICATIONS

Shimamoto et al, Nature, vol. 338, pp. 274–276 (Mar. 16, 1989).
Tanaka et al, Nucleic Acids Research, vol. 18, No. 23, pp. 6767–6770 (1990).
Baba et al, Plant Cell Physiol., 27(3), pp. 463–471 (1986).
Ueki et al, Plant Cell Physiol., 36(5), pp. 903–914 (1995).
Burnell, Plant Cell Physiol., 31(2), pp. 295–297 (1990).
Matsuoka et al. (1988) Primary Structure of Maize Pyruvate, Orthophosphate Dikinase as Deduced from cDNA Sequence, J. Biol. Chem. 263 (23): 11080–11083, Aug. 15, 1988.
Rosche et al. (1990) Primary structure of pyruvate, orthophosphate dikinase in the dicotyledonous C4 plant *Flaveria trinervia*, FEBS Letters 273 (1,2): 116–121, Oct. 1990.
Pocalyko et al. (1990) Analysis of Sequence Homologies in Plant and Bacterial Pyruvate Phosphate Dikinase, Enzyme I of the Bacterial . . . , Biochem. 29: 10757–10765, Nov. 1990.
Rosche et al. (1994) Primary structure of the photosynthetic pyruvate orthophosphate dikinase of the C3 plant *Flaveria pringlei* and . . . , Plant Molecular Biology 26: 763–769, Oct. 1994.
Rudinger, J. (1976) Characteristics of the amino acids as components of a peptide hormone sequence, In Peptide Hormones, Ed. J. A. Parsons, University Park Press, pp. 1–7, Jun. 1976.

*Primary Examiner*—Robert A. Wax
*Assistant Examiner*—Einar Stole
*Attorney, Agent, or Firm*—Birch, Stewart, Kolasch & Birch, LLP

[57] ABSTRACT

As means for giving cold-stability to plants, a novel polypeptide having cold-stable pyruvate, orthophosphate dikinase activity, a cloned DNA encoding the same, and a recombinant vector containing the DNA are disclosed. The polypeptide according to the present invention has cold-stable pyruvate, orthophosphate dikinase activity, which has an amino acid sequence that is the same as the amino acid sequence of ⅙ region of the entire region from the C-terminal of the following polypeptide (1) or (2), except that at least one amino acid residues of said ⅙ region are substituted with other amino acid residues:

(1) a pyruvate, orthophosphate dikinase having an amino acid sequence shown in SEQ ID NOS. 1–10 in Sequence Listing; and (2) a polypeptide having an amino acid sequence which has a homology of not less than 50% with the amino acid sequence mentioned in (1), said polypeptide having cold-stable pyruvate, orthophosphate dikinase activity.

8 Claims, 3 Drawing Sheets

POLYPEPTIDE HAVING COLD-STABLE PYRUVATE, ORTHOPHOSHATE DIKINASE ACTIVITY, DNA ENCODING THE SAME AND RECOMBINANT VECTOR AND TRANSFORMED PLANTS CONTAINING THE DNA

TECHNICAL FIELD

The present invention relates to a novel polypeptide having cold-stable pyruvate, orthophosphate dikinase (hereinafter also referred to as "PPDK") activity, a cloned DNA encoding the same and a recombinant vector containing the DNA, as means for giving cold-stability to plants. The present invention also relates to plants transformed with the DNA according to the present invention.

BACKGROUND ART $C_4$ plants have high abilities of photosynthesis under the conditions of strong light, high temperature or low $CO_2$. However, their photosynthesis abilities are largely reduced under low temperature except for those which are adapted to low temperature conditions. Although PPDK (EC 2.7.9.1, that catalyzes the reaction in which AMP, phosphoenol pyruvate and pyrophosphate are produced from ATP, pyruvate and orthophosphate) is one of the important enzymes in $C_4$ path, its activity is not sufficient with respect to the photosynthesis rate in leaf tissue, so that it is one of the enzymes which determine the rate of $CO_2$ fixation in $C_4$ photosynthesis. Further, it has been pointed out simultaneously with the discovery of this enzyme that this enzyme is cold-sensitive. In case of maize PPDK, the enzyme activity has a point of inflection at 11.7° C. This temperature is coincident with the limit temperature of growth of maize. From these, it is thought that PPDK is one of the causes which reduce the photosynthesis rate of $C_4$ plants at low temperature. Therefore, by improving the cold-sensitivity of PPDK, the limit temperature of growth of maize may be lowered. *Flaveria brownii* which is a plant belonging to the family Compositae is classified into $C_3/C_4$ intermediate type, and it is known that its PPDK is not substantially inactivated by low temperature treatment at 0° C. (Burnell JN: A comparative study of the cold-sensitivity of pyruvate, Pi dikinase in Flaveria species. Plant Cell Physiol. 31, 295–297 (1990)).

By cloning the gene encoding the cold-stable PPDK of *Flaveria brownii,* and by transforming a plant with the gene, it is expected that resistance to coldness can be given to the plant.

DISCLOSURE OF THE INVENTION

Accordingly, an object of the present invention is to provide a novel polypeptide having cold-stable PPDK activity, a cloned DNA encoding the same and a recombinant vector containing the DNA, as means for giving cold-stability to plants. Another object of the present invention is to provide a plant transformed with the above-mentioned DNA according to the present invention.

The present inventors intensively studied to succeed in cloning the complete PPDK gene of *Flaveria brownii,* determining the nucleotide sequence of the gene and the amino acid sequence encoded thereby, and in identifying the region in the PPDK gene, which gives cold-stability, thereby completing the present invention.

That is, the present invention provides a polypeptide having cold-stable PPDK activity, which has an amino acid sequence that is the same as the amino acid sequence of ⅙ region of the entire region from the C-terminal of the following polypeptide (1) or (2), except that at least one amino acid residues of said ⅙ region are substituted with other amino acid residues:

(1) a PPDK having an amino acid sequence shown in SEQ ID NO. 1 to 4 in Sequence Listing; and (2) a polypeptide having an amino acid sequence which has a homology of not less than 50% with the amino acid sequence mentioned in (1), said polypeptide having cold-stable PPDK activity.

The present invention also provides a cloned DNA encoding the polypeptide having cold-stable PPDK activity according to the present invention. The present invention further provides a recombinant vector containing the DNA according to the present invention, which can express in a host a polypeptide having cold-stable PPDK activity. The present invention still further provides a plant which is transformed with the DNA according to the present invention.

By the present invention, a gene encoding PPDK having cold-stability was cloned and sequenced. Further, the region in the gene, which gives cold-stability was also identified. Therefore, by transforming a plant having cold-sensitive PPDK with the gene according to the present invention, the cold-sensitive PPDK may be changed to cold-stable PPDK. Further, by incorporating the above-mentioned cold-stability-giving region into the corresponding region of a cold-sensitive PPDK, the cold-sensitive PPDK may be changed to cold-stable PPDK. By this, the plant can be cultivated at a cold area in which the plant could not be hitherto cultivated. Therefore, it is expected that the present invention will much contribute to agriculture.

BEST MODE FOR CARRYING OUT THE INVENTION

Figure 1:
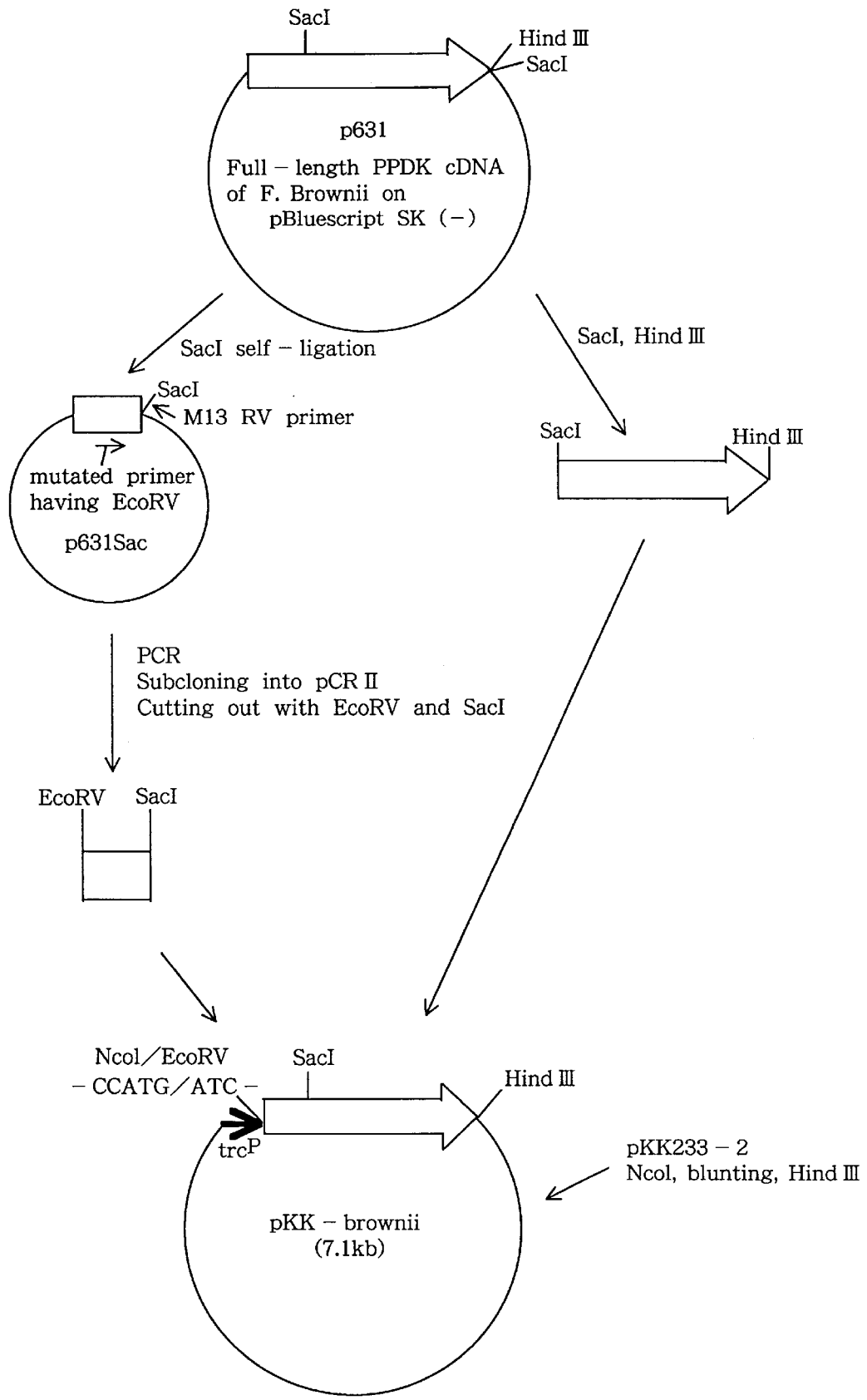
FIG. 1 schematically shows a construction method of an expression vector containing an example of the PPDK gene according to the present invention.

By the present invention, the gene of PPDK having cold-stability of *Flaveria brownii* was cloned and its nucleotide sequence and the deduced amino acid sequence encoded thereby were determined. The nucleotide sequence and the amino acid sequence are shown in SEQ ID NOS. 9–10 in Sequence Listing. As described in detail in the following examples, this sequence was determined by extracting the total RNAs from leaves of *Flaveria brownii;* preparing a cDNA library according to a conventional method; carrying out plaque hybridization method using a probe prepared by referring to the region of PPDK gene of *Flaveria bidentis* and the region of PPDK gene of maize, which regions have high homology; selecting and cloning positive clones; and sequencing the gene by dideoxy method. The sequence has high homology with the PPDK gene of *Flaveria bidentis* belonging to the same genus, and has a relatively high homology with the maize PPDK gene. Further, the sequences of the N-terminal region, C-terminal region and internal regions of the deduced amino acid sequence are completely the same as the corresponding sequences of the PPDK of *Flaveria brownii* directly purified from green leaves of this plant. Therefore, it is apparent that the cloned gene is the PPDK gene of *Flaveria brownii*. The PPDK gene of *Flaveria bidentis* was sequenced by carrying out plaque hybridization using maize cDNA as the probe; cloning the positive clones; and sequencing the gene by dideoxy method.

The amino acid sequence shown in SEQ ID NOS. 9 and 10 is novel and 40 amino acid residues thereof are different from the amino acid sequence of the PPDK of *Flaveria bidentis* belonging to the same genus. About 180 amino acid residues thereof are different from the amino acid sequence of the maize PPDK. Thus, in spite of the fact that the amino acid sequence of PPDK of *Flaveria brownii* shown in SEQ. ID NOS. 9 and 10 has a high homology with the amino acid sequence of the PPDK of *Flaveria bidentis* belonging to the same genus, the PPDK of *Flaveria bidentis* is cold-sensitive while that of *Flaveria brownii* is cold-stable. Thus, the small difference in amino acid residues brings about the important difference of the character. The present invention provides a cloned PPDK gene encoding the amino acid sequence shown in SEQ ID NOS. 9 and 10. As mentioned above, this amino acid sequence is novel and has a prominent effect that it has cold-stability. The gene according to the present invention is not restricted to that having the nucleotide sequence shown in SEQ ID NO. 9, but any nucleotide sequence which encodes this amino acid sequence is within the scope of the gene according to the present invention.

The present inventors tried to identify the region in the PPDK gene of *Flaveria brownii* shown in SEQ ID NO. 9, which region gives cold-stability. That is, as described in detail in the following examples, the PPDK gene of *Flaveria brownii* was divided into three regions having about the same size by restriction enzymes; each of the regions was exchanged with the corresponding region of maize PPDK gene to form chimeric PPDK genes; and whether the PPDKs encoded by the obtained chimeric genes have cold-stability or not was determined. As a result, it was confirmed that the region giving cold-stability exists in the last ⅓ region of the PPDK gene of *Flaveria brownii*. Further, this last ⅓ region was divided by a restriction enzyme into two regions having about the same size, and which region contains the region giving cold-stability was determined by the similar method. As a result, it was confirmed that the function to give cold-stability is encoded in the region downstream of the Xho I site of the PPDK gene of *Flaveria brownii* shown in SEQ ID NO. 9. That is, it was confirmed that the function to give cold-stability is located within the amino acid sequence between the 832nd amino acid residue, arginine, and the 955th amino acid residue, valine, of the amino acid sequence shown in SEQ ID NOS. 9 and 10 (the amino acid sequence from the 832nd amino acid residue to the 955th amino acid residue may be hereinafter referred to as "cold-stability-giving sequence").

That is, it was proved that the region relating to cold-stability of PPDK is located in the ⅙ region of the entire region from the C-terminal. On the other hand, in SEQ ID NOS. 1 and 2 in Sequence Listing, the nucleotide sequence of the gene encoding PPDK of *Flaveria bidentis* and deduced amino acid sequence encoded thereby are shown, and in SEQ ID NOS. 3 and 4, the nucleotide sequence of the gene encoding PPDK of maize and deduced amino acid sequence encoded thereby are shown (Journal of Biochemistry 263, 11080–11083 (1988)). In SEQ ID NOS. 5 and 6, the nucleotide sequence of the gene encoding PPDK of *Bacteroides symbiosus* which is a bacterium, and deduced amino acid sequence encoded thereby are shown (Biochemistry 29, 10757–10765 (1990)). In SEQ ID NOS. 7 and 8, the nucleotide sequence of the gene encoding PPDK of *Entamoeba histolytica* which is a bacterium, and deduced amino acid sequence encoded thereby are shown (Molecular and Biochemical Parasitology 62, 153–156 (1993)). As described above, it was proved by the present invention that the region relating to cold-stability of PPDK is located in the ⅙ region of the entire region from the C-terminal, it is possible to obtain cold-stable PPDK by substituting at least one amino acid residue in the ⅙ region of the entire region from the C-terminal of the amino acid sequence shown in SEQ ID NOS. 1–2, 3–4, 5–6 or 7–8. Here, the term "cold-stable" means that activity of the enzyme after leaving the enzyme to stand at 0° C. for 20 minutes is not less than 60% of the original activity.

As mentioned above, since the region from the 832nd amino acid residue, arginine, to the 955th amino acid residue, valine, in the amino acid sequence shown in SEQ ID NOS. 9 and 10 defines cold-stability, the cold-sensitive PPDKs having the amino acid sequence shown in SEQ ID NOS. 1–8 can be converted to cold-stable PPDKs by substituting the corresponding regions of the cold-sensitive PPDKs with the amino acid sequence from the 832nd amino acid residue, arginine, to the 955th amino acid residue, valine, of the amino acid sequence shown in SEQ ID NOS. 9 and 10. This finding is very important because by utilizing this, any desired cold-sensitive PPDK can be converted to a cold-stable PPDK. The method of giving cold-stability to a PPDK is not restricted to the method as described in the examples below, in which the cold-stability-giving sequence of PPDK of *Flaveria brownii* is exchanged with the corresponding region of a cold-sensitive PPDK to prepare a chimeric gene, but the cold-stability may be given by changing the corresponding region of a cold-sensitive PPDK of a plant to the same sequence as the cold-stability-giving sequence of *Flaveria brownii* by site-directed mutagenesis. Therefore, any DNA which encodes a polypeptide having PPDK activity, which contains the above-described cold-stability-giving sequence is within the scope of the present invention. In particular, the PPDK in which the 869th amino acid residue in the amino acid sequence shown in SEQ ID NOS 1 and 2 is substituted by proline, and the PPDK in which the 885th and 952nd amino acid residues in the amino acid sequence shown in SEQ ID NOS. 1 and 2 are substituted by leucine and valine, respectively, have cold-stability.

The PPDKs to which cold-stability is to be given are not restricted to those shown in SEQ ID NOs. 1–8, but may be those having not less than 50% of homologies to the sequences shown in SEQ ID NOs. 1–8. Preferably, the nucleotide sequence of the gene encoding a PPDK to which cold-stability is to be given has a homology to the PPDK gene of *Flaveria brownii* in an amount of not less than 48.5%, more preferably, not less than 90%.

It is well-known in the art that there are cases wherein the physiological activity of a physiologically active peptide is retained even if the amino acid sequence of the peptide is modified to a small extent, that is, even if one or more amino acids in the amino acid sequence are substituted or deleted, or even if one or more amino acids are added to the amino acid sequence. Therefore, polypeptides having the same amino acid sequence as shown in SEQ ID NOS. 9 and 10 except that the polypeptides have such modifications, which have cold-stable PPDK activity, are included within the scope of the present invention. That is, the polypeptides having the same amino acid sequence as shown in SEQ ID NOS 9 and 10 except that one or more amino acids are added, deleted or substituted, which have cold-stable PPDK activity, are included within the scope of the present invention. Similarly, DNAs having the same nucleotide sequence as shown in SEQ ID NOS. 9 and 10 except that one or more nucleotides are added, deleted or substituted, which encode polypeptides having cold-stable PPDK activity, are also within the scope of the present invention.

Modification of DNA which brings about addition, deletion or substitution of the amino acid sequence encoded thereby can be attained by the site-specific mutagenesis which is well-known in the art (e.g., Nucleic Acid Research, Vol. 10, No. 20, p6487–6500, 1982). In the present specification, "one or more amino acids" means the number of amino acids which can be added, deleted or substituted by the site-specific mutagenesis.

Site-specific mutagenesis may be carried out by, for example, using a synthetic oligonucleotide primer complementary to a single-stranded phage DNA except that the desired mutation as follows. That is, using the above-mentioned synthetic oligonucleotide as a primer, a complementary chain is produced by a phage, and host bacterial cells are transformed with the obtained double-stranded DNA. The culture of the transformed bacterial cells is plated on agar and plaques are formed from a single cell containing the phage. Theoretically, 50% of the new colonies contain the phage having a single-stranded chain carrying the mutation and remaining 50% of the colonies contain the phage having the original sequence. The obtained plaques are then subjected to hybridization with a kinase-treated synthetic probe at a temperature at which the probe is hybridized with the DNA having exactly the same sequence as the DNA having the desired mutation but not with the original DNA sequence that is not completely complementary with the probe. Then the plaques in which the hybridization was observed are picked up, cultured and the DNA is collected.

In addition to the above-mentioned site-specific mutagenesis, the methods for substituting, deleting or adding one or more amino acids without losing the enzyme activity include a method in which the gene is treated with a mutagen and a method in which the gene is selectively cleaved, a selected nucleotide is removed, added or substituted and then the gene is ligated.

By transforming a plant with PPDK gene of *Flaveria brownii* or with a DNA encoding a polypeptide containing the cold-stability-giving sequence, which has PPDK activity, a cold-resistant plant can be obtained. Preferred examples of the plants to be transformed include maize, sugar cane, millet, barnyard grass and sorghum, although not restricted thereto.

Methods for transforming plants have already been established and the method utilizing *Agrobacterium tumefaciens* may preferably be employed. The method for transforming plants utilizing *Agrobacterium tumefaciens* is well-known in the art. By this method, both dicotyledons (e.g., Japanese Laid-open Patent Application (Kokai) No. 4-330234) and monocotyledons (WO 94/00977) can be transformed. Alternatively, the DNA may be introduced into plant protoplasts by electroporation method or the like well-known in the art. Further, transformation may also be carried out by attaching the DNA to tungsten particles and the like and implanting the particles in embryos of a plant. Concrete methods of these transformation methods are described in the examples hereinbelow described.

EXAMPLES

The present invention will now be described more concretely by way of examples thereof. However, the present invention is not restricted to the examples below.

1. Cloning and Sequencing of PPDK Gene of *Flaveria brownii*

(1) Preparation of cDNA Library and Cloning of Full-length cDNA (i) Preparation of cDNA Library From green leaves (60 g) of *F. brownii*, total RNAs were isolated by the guanidine hydrochloride/phenol method. By this method, 26.5 mg of RNA after lithium precipitation was obtained. Then 118.9 μg of poly(A) $^+$RNA was obtained from 13.2 mg of the RNA according to a conventional method using a column containing Oligo dT cellulose Type 7 (commercially available from PHARMACIA). For the preparation of the cDNA library, TimeSaver cDNA Synthesis kit (commercially available from PHARMACIA), Lambda ZAPII vector (commercially available from STRATAGENE) and the packaging reagent attached to cDNA cloning system λgt10 (commercially available from AMERSHAM) were used. Using an EcoRI/NotI linker, a cDNA library in which DNA fragments are inserted into the EcoRI site of Lambda ZAPII vectors was prepared. The size of the prepared cDNA library was 415,000 pfu. As the host cells, XL1-Blue cells were used.

(ii) Preparation of Probe

Using a primer having the sequence of 5":GACG-GCTAAAAAGAGGGT (SEQ ID NO. 12) (designed based on the regions of PPDK of *Flaveria bidentis* and of maize PPDK, which have a high homology) and a R primer having the sequence of TATCGAGAAACCTTCTATAC (SEQ ID NO. 13) (a part of the sequence of PPDK of *Flaveria bidentis*, complementary chain), a DNA fragment originated from RNA of *F. brownii* was amplified by reverse transcription PCR, and the amplified DNA fragment was inserted in pCRII vector (commercially available from INVITROGEN). Using the obtained vector as a template, and using the same primers as mentioned above, the DNA was amplified and the PCR product was subjected to electrophoresis, followed by recovering the DNA from the gel by using SUPREC-01 (commercially available from TAKARA SHUZO). By this process, a DNA fragment having a size of 428 bp starting from the 24th bp downstream of the N-terminal of the mature protein can be obtained. This fragment was labelled with $^{32}$P using Multiprime DNA labelling system (commercially available from AMERSHAM) to prepare a probe.

(iii) Cloning of Full-length cDNA of *Flaveria brownii*

The cDNA library was screened by the plaque hybridization method using the above-mentioned DNA fragment as a probe. As the hybridization filter, Hybond N$^+$ (AMERSHAM) was used, and the hybridization was carried out in 6×SSC containing 5×Denhalt's solution, 0.1% SDS and 100 μg/ml of denatured salmon testis DNA at 65° C. overnight. Washing was performed with 2×SSC containing 0.1% SDS at room temperature for 5 minutes; with 2×SSC containing 0.1% SDS at room temperature for 90 minutes; and 1×SSC containing 0.1% SDS at 68° C. for 90 minutes. By this, 28 independent positive clones were obtained. From these, 11 plaques which showed strong signals were selected and subjected to second screening. The second screening was carried out in the same manner as in the first screening except that the time of the second washing was 60 minutes. As a result, independent positive plaques originated from a single phage were obtained from 6 clones. To check the sizes of the inserted DNA fragments, PCR was carried out using the above-described R primer, M13PrimerM4 (GTTTTCCCAGTCACGAC, (SEQ ID NO. 13) commercially available from TAKARA SHUZO) and M13PrimerRV (CAGGAAACAGCTATGAC, (SEQ ID NO. 14) TAKARA SHUZO) as primers and using the phage as a template. As a result, 2 clones contained the full-length cDNA. Thereafter, by in vivo excision, the inserted DNA fragments were subcloned into a plasmid vector pBluescriptIISK(-) (commercially available from STRATAGENE). The recombinant plasmids obtained by the subcloning were named p411 and p631.

It was found by the above-described PCR that the library prepared as described above was a library containing sufficiently long inserts, which was suited for cDNA screening. Thus, for the isolation of mRNAs of *Flaveria brownii,* it is advantageous to employ the above-described method and to obtain a large amount of mRNAs at once by treating a large amount of RNAs as described above.

Further, since the above-described cDNA library contains a number of inserts which are sufficiently long, screening of the full-length cDNA was able to be performed easily by preparing a probe prepared by using a primer which hybridizes with a region in the vicinity of the processing region of the desired protein.

(2) Determination of Total Nucleotide Sequence of cDNA and Comparison of Deduced Amino Acid Sequence To determine the total nucleotide sequence of the inserted cDNA fragment of p631, deletion mutants were prepared. The deletion mutants were prepared by using Deletion Kit for Kilo-Sequence (commercially available from TAKARA SHUZO). However, the reaction by exonuclease III was stopped by transferring the reaction mixture to Mung Bean Nuclease buffer kept at 65° C. Determination of the nucleotide sequence was carried out using a plasmid purified by using Qiagen Plasmid Mini Kit (commercially available from Diagen), Taq DyeDeoxy Terminator Cycle Sequencing Kit (commercially available from ABI) and Applied Biosystems 373A DNA Sequencer (ABI). Both chains were sequenced except for some parts thereof. Based on the determined nucleotide sequence, amino acid sequence was determined. The determined nucleotide sequence and the amino acid sequence are shown in SEQ ID NO. 5 in the Sequence Listing.

It should be noted that in the preparation of the deletion clones for sequencing the isolated cDNA, it was important to preliminarily heat the Mung Bean Nuclease Buffer at 65° C. because the reaction could not be stopped by merely transferring the reaction mixture to the Mung Bean Nuclease Buffer. Further, since the sequence at the region up to about 600–900 bp from the boarder between the vector and the insert could not be determined by deleting the insert from the upstream end alone, it was necessary to carry out the deletion from both ends.

On the other hand, PPDK was purified directly from *Flaveria brownii* and the amino acid sequences of its N-terminal region, C-terminal region and internal regions were determined. The PPDK was purified as follows. That is, green leaves were ground in triple volume of extraction buffer. After centrifugation, ammonium sulfate was added to the supernatant to 30% saturation and precipitated proteins were removed. Ammonium sulfate was further added to 70% saturation and precipitated proteins were recovered. The recovered proteins were applied to Sephadex G25 (commercially available from PHARMACIA) to remove salts. The resultant was applied to DEAE-Sepharose column (PHARMACIA) and the proteins adsorbed to the column were eluted by KCl having a gradient of 50–400 mM. Fractions having PPDK activity were combined and concentrated by ammonium sulfate of 70% saturation, followed by desalination by Sephadex G25. The resultant was then applied to a hydroxyapatite column. The adsorbed proteins were eluted by phosphate buffer having a gradient of phosphate from 10 mM to 40 mM. Fractions having PPDK activity were combined and concentrated by ammonium sulfate of 70% saturation, followed by desalination by Sephadex G25. The resultant was subjected to SDS-PAGE and the band of PPDK was cut out. Protein was recovered from the gel by electroelution. By this process, purified PPDK sample was obtained in an amount of about 5–10 nmol. The purified PPDK thus obtained showed a single band in SDS-PAGE.

Then the amino acid sequences of N-terminal region, C-terminal region and internal regions of the thus obtained purified PPDK were determined. That is, the amino acid sequence of the N-terminal region was determined by transferring the protein on a PVDF membrane and then determining the sequence using a gas phase amino acid sequencer. The amino acid sequence of the C-terminal region was determined by digesting the purified PPDK with carboxypeptidase Y and estimating the amino acid sequence based on the relationship between the composition of the liberated amino acids and the digestion time. The amino acid sequences of the internal regions were determined by determining the amino acid sequence from the N-terminal of peptides generated by digesting the protein with a protease. The details of this method are as follows. Firstly, as in the case of determining the amino acid sequence of the N-terminal region, PPDK from green leaves of *Flaveria brownii* was partially purified and subjected to an ordinary SDS-PAGE. The gel was stained with Coomasssie Brilliant Blue R250 and the band of PPDK was cut out. The cut out gel was equilibrated in an equilibrating buffer (Tris-HCl pH6.8, 125 mM, EDTA 1 mM, 0.1% SDS) and inserted in a well, followed by second SDS-PAGE. Here, an overlaying solution (Tris-HCl pH6.8, 125 mM, EDTA 1 mM, 0.1% SDS, 0.01% BPB, 20% glycerol) and an enzyme solution (Tris-HCl pH6.8, 125 mM, EDTA 1 mM, 0.1% SDS, 0.01% BPB, 10% glycerol, lysyl endopeptidase 1–15 $\mu$g or V8 protease 0.01–0.1 $\mu$g) were added together with the equilibrated gel. After carrying out electrophoresis for a while, digestion of the protein was carried out in the concentrated gel (the electric power was turned off and the gel was left to stand for 45 minutes). Then electrophoresis was restarted and the resultant was transferred to a PVDF membrane in the same manner as in the determination of the N-terminal sequence, and the amino acid sequences of the fragments obtained by the digestion were determined from the N-terminals thereof using the gas phase amino acid sequencer.

The determined sequences of N-terminal region, C-terminal region and internal regions are as follows:

N-terminal Sequence: Asn Pro Val Ser Pro Pro Val (72–78)

C-terminal Sequence: Leu - Ala Ala * - Val Val (948–955)

Internal Sequence (1): Lys Leu Tyr Glu Phe Leu Val Asn Ala Gln Gly - Aspp Val Val Ala, (349–365)

Internal Sequence (2): Gln Leu Leu Ala Pro Pro Ala Met Ser, Asn Ala Leu - Thr (592–605)

Internal Sequence (3): Leu Thr Ala Asp Thr Gly Met Ser Lys, Asp Glu Ile Tyr Ser Arg Ile Glu (721–738)

Internal Sequence (4): Ala - - - Ser Phe Gly Thr Asn Asp Leu Cys Gln Met Val Phe Gly - Ser (844–862)

In the above-described amino acid sequences, "*" means glutamine but could not be analyzed by the analyzer used, and "-" means that the result of the analysis was unclear. The numbers in the parentheses indicate the amino acid number of the corresponding region in the amino acid sequence shown in SEQ ID NOS 9 and 10. Although parts of the Internal Sequences (2) and (4) are different from the amino acid sequence shown in SEQ ID NOS. 9 and 10, it is thought that this is due to errors of the amino acid sequencer. As is well-known, errors are caused by amino acid sequencers at considerable frequency while errors are not substantially caused by DNA sequencers.

Since the amino acid sequence shown in SEQ ID NOS. 9 and 10 well corresponds with the partial amino acid sequences directly determined in the above-described purified PPDK, it was confirmed that the amino acid sequence shown in SEQ ID NOS. 9 and 10 is the amino acid sequence of PPDK. The amino acid sequence shown in SEQ ID NOS. 9 and 10 was compared with the amino acid sequences of known PPDKs of *Flaveria bidentis* and maize. As a result, 40 amino acid residues (*Flaveria bidentis*) and about 180 amino acid residues (maize) were different, respectively, in the mature protein region. Further, from the above-described results, it is thought that in the amino acid sequence shown in SEQ ID NOS. 9 and 10, the amino acid sequence from 1st to 71st amino acid residue does not exist in the mature protein but a transit peptide necessary for passing through membranes, which is processed after passing through membranes. Differences between the amino acid sequences of mature proteins of *Flaveria brownii* and *Flaveria bidentis* are shown in Table 1 below.

TABLE 1

Amino Acid Numbers and Amino Acids Which are Different

| brownii | bidentis |
|---------|----------|
| 5 Phe   | 6 Ser    |
| 10 Pro  | 11 Leu   |
| 15 Asn  | 16 Arg   |
| 28 Thr  | 29 Asn   |
| 40 Pro  | 41 Ser   |
| 41 Ala  | 42 Ser   |
| 48 Arg  | 47 Leu   |
| 49 Arg  | 48 Thr   |
| 50 Lys  | 49 Pro   |
| 52 Ser  | 50 Ala   |
| 57 Ile  | 55 Pro   |
| 61 Thr  | 59 Ser   |
| 62 Gly  | 60 Ser   |
| 66 Leu  | 64 Pro   |
| 81 Thr  | 79 Ala   |
| 92 Asn  | 90 Arg   |
| 97 Lys  | 95 Arg   |
| 114 Ala | 112 Ser  |
| 146 Lys | 138 Ser  |
| 150 Leu | 148 Ser  |
| 154 Gln | 152 Asp  |
| 170 Ala | 168 Pro  |
| 201 Asp | 199 Ala  |
| 205 Ala | 203 Gly  |
| 263 Ala | 261 Val  |
| 265 Gln | 263 Lys  |
| 323 Cys | 321 Ser  |
| 356 Val | 354 Ile  |
| 374 Val | 372 Gly  |
| 382 Glu | 380 Asp  |
| 385 Arg | 383 Lys  |
| 392 Val | 390 Glu  |
| 396 Arg | 394 Gly  |
| 465 Asn | 463 Asp  |
| 490 Val | 488 Cys  |
| 564 Val | 562 Ile  |
| 583 Ser | 581 Thr  |
| 605 Thr | 603 Ile  |
| 672 Ala | 670 Val  |
| 723 Thr | 721 Ala  |
| 724 Ala | 722 Val  |

TABLE 1-continued

Amino Acid Numbers and Amino Acids Which are Different

| brownii | bidentis |
|---------|----------|
| 730 Lys | 728 Ala  |
| 736 Arg | 734 Lys  |
| 739 Lys | 737 Asn  |
| 777 Asn | 775 Thr  |
| 803 Gly | 801 Ser  |
| 818 Leu | 816 Val  |
| 838 Asp | 836 Glu  |
| 841 Ala | 839 Gly  |
| 845 Glu | 843 Asp  |
| 871 Pro | 869 Gln  |
| 875 Ser | 873 Ala  |
| 887 Leu | 885 Ile  |
| 954 Val | 952 Ile  |

2. Production of PPDK of *Flaveria brownii* in *E. coli* and Measurement of Cold-stability To confirm that a cold-stable enzyme is actually produced from the cDNA of PPDK of *Flaveria brownii* isolated as described above, expression in *E. coli* was carried out as follows:

To remove the transit peptide and to ligate the DNA to an expression vector so that the reading frames are coincident, restriction sites were introduced as follows: That is, p631 was digested with SacI and recyclized to obtain p631Sac (a plasmid same as p631 except that downstream region of SacI site is deleted). PCR was performed using p631Sac as a template and using primer 4: GATATCAATCCGGT-GTCTCCTCC (SEQ ID NO. 15) containing EcoRV site, prepared based on the sequence in the vicinity of the processing region and primer M13 RV (commercially available from TAKARA SHUZO) complementary to the sequence of the vector, and the amplified fragment was subcloned into pCR II. A fragment containing the N-terminal region was cut out using restriction enzymes EcoRV and SacI. Three DNA fragments, that is, the thus cut out DNA fragment, the SacI-HindIII fragment from p631 (containing the remaining region of cDNA of PPDK) and a fragment obtained by digesting pKK233–2 with NcoI, blunting the ends with Klenow fragment and then digesting the resultant with HindIII, were ligated (FIG. 1). *E. coli* MV1184 was transformed with the obtained plasmid and used for expression experiments. One ml of a precultured medium was diluted with 9 ml of fresh LB medium (containing 50 mg/l of ampicillin) and the resultant was cultured with shaking for 3 hours at 37° C. Then IPTG was added to a concentration of 5 mM and culture was continued for another 3 hours, followed by collection of cells by centrifugation. The cells were suspended in 0.5 ml of an extraction buffer (50 mM Hepes-KOH pH7.5, 10 mM MgSO$_4$, 1 mM EDTA, 5 mM DTT) and lysozyme was added to a final concentration of about 0.5 mg/ml. The suspension was left to stand in ice for 5 minutes and then treated by an ultrasonic disrupter (Model UCD-130T commercially available from COSMOBIO) for a period of 30 seconds each, totally 5 minutes, thereby extracting the enzyme. The resultant was centrifuged by a microcentrifuge for 10 minutes and the supernatant was applied to Sephadex G25 column equilibrated with a column buffer (50 mM Hepes-KOH pH 7.0, 10 mM MgCl$_2$, 2 mM EDTA, 10 mM DTT) to remove low molecular substances. The resultant was left to stand at 25° C. for not less than 30 minutes thereby carrying out association to tetramer, which was then used for the measurement of activity.

Figure 2:
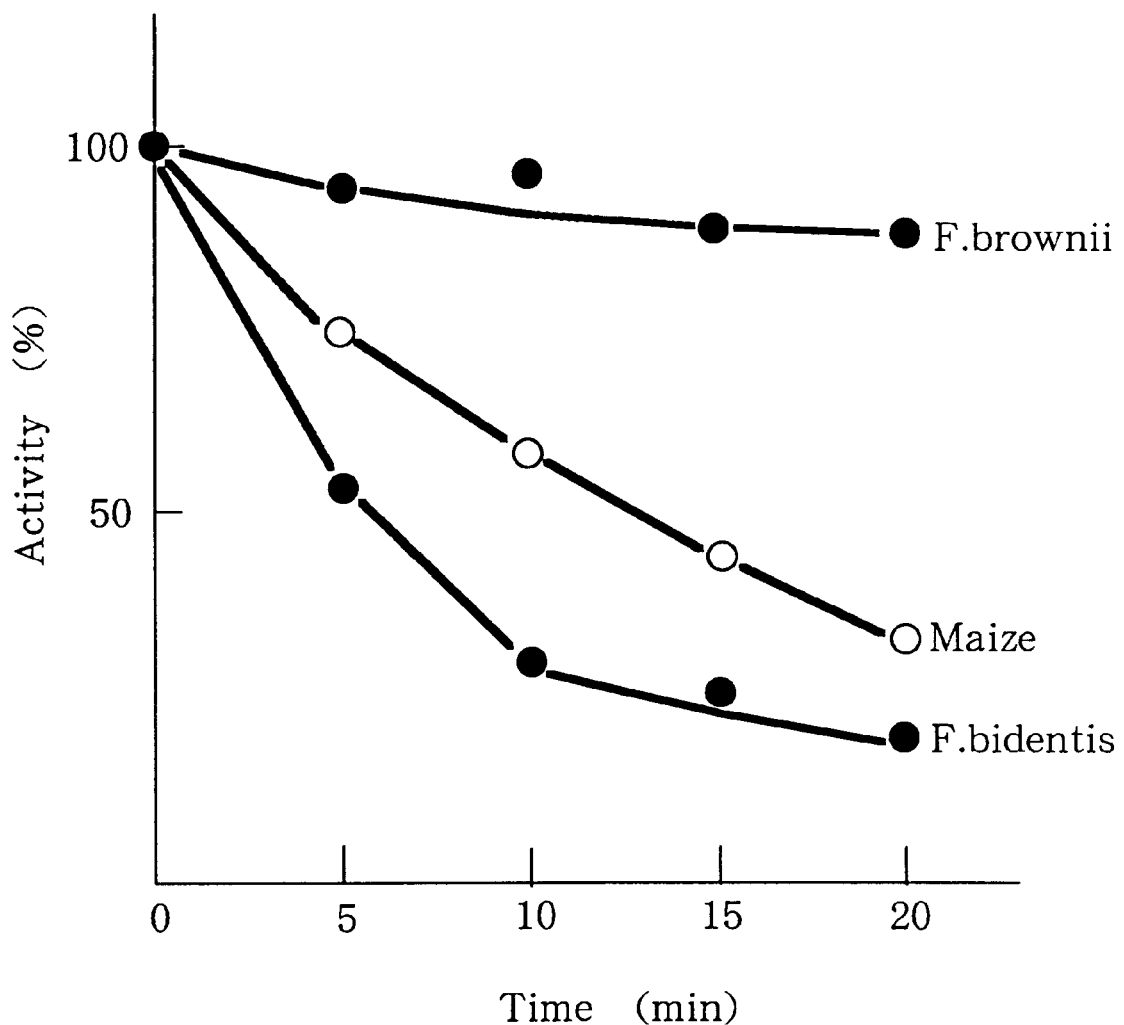
FIG. 2 shows the change in enzyme activity with time when PPDKs of *Flaveria brownii, Flaveria bidentis* and maize, which were expressed in *Escherichia coli,* were kept at 0° C.

The PPDKs produced in E. coli cells from PPDK cDNAs of Flaveria brownii, Flaveria bidentis and maize (Harvest Queen) exhibited substantially the same mobility as the enzymes originated from the plants in SDS-PAGE. Although the molecular weights of the mature enzymes, which are expected from the respective cDNAs are about the same, the apparent molecular weights on SDS-PAGE substantially differ. It was proved that this is due to the differences in amino acid compositions and not due to deletion processing of the proteins or modifications after translation, such as attaching of sugar chains. The cold-stability of each PPDK produced in E. coli was identical to the corresponding enzyme originated from each plant. Thus, the cold-stability of the PPDK of Flaveria brownii is attained without an auxiliary factor specific to the plant or processing after translation, so that it is expected that cold-stable PPDK is produced by introducing the cDNA into maize and expressing it. FIG. 2 shows the relationship between the time which lapsed after placing the enzyme at 0° C. and relative activity of PPDK.

In the above-described process for producing active PPDK in E. coli, the cDNA from which the region encoding the transit peptide was removed was inserted in the expression vector. For this, it was important to precisely match the site to be cut with the site corresponding to the N-terminal of the enzyme originated from the plant.

|  | Amount of Enzyme Produced in E. coli | Primer Used |
|---|---|---|
| (F. brownii) | | |
| MITAKKRVFTF . . . | − | 2 |
| MIPVSPPVTTTKKRVFTF . . . | + | 3 |
| MINPVSPPVTTTKKRVFTF . . . | ++ | 4 |
| NPVSPPVTTTKKRVFTF . . . | (enzyme originated from leaves) | |
| (F. bidentis) | | |
| MITAKKRVFTF . . . | ++ | |
| MIPVSPPVTTAKKRVFTF . . . | − | |
| TAKKRVFTF . . . | (enzyme originated from leaves) | |
| (maize) | | |
| MATKKRVFTF . . . | ++ | |
| TTKKRVFTF . . . | (enzyme originated from leaves) | |

More particularly, at the time point of carrying out the expression experiment of cDNA of Flaveria brownii, expression of PPDKs of maize and Flaveria bidentis had been succeeded, referring to the cutting site in maize in both cases. Thus, in expression of cDNA of Flaveria brownii too, firstly, the DNA was cut at the same site using primer 2 and it was tried to express the cDNA after constructing an expression vector containing the cDNA. However, PPDK was not produced at all. Then, based on the sequence of the N-terminal region of the enzyme originated from leaves, an expression vector in which the inserted cDNA contains an additional sequence encoding the enzyme extended to the direction of N-terminal by 7 residues was constructed using the primer 3 and expression was carried out using the expression vector. As a result, production of PPDK was confirmed. However, even with this expression vector, the amount of the produced enzyme was small, so that the enzyme was not obtained in an amount sufficient for measuring its activity. Thus, an expression vector in which the inserted cDNA contains a still additional sequence encoding the enzyme extended to the direction of N-terminal by 1 residue was constructed using the primer 4 and expression was carried out using the expression vector. As a result, a large amount of PPDK was produced and its cold-stability was confirmed. The nucleotide sequences of the primer 2 and the primer 3 were as follows:

primer 2: CGGTGTCTCCTCCGGATATCACG-GCTAAAAAGAG (SEQ ID NO. 16)
   primer 3: TTGATATCCCGGTTGTCTCCTCCGGTA (SEQ ID NO. 17)

3. Identification of Region Giving Cold-stability in PPDK Gene of Flaveria brownii (1) Chimera of Flaveria brownii and Flaveria bidentis The expression vectors were recombined according to a conventional method using restriction enzymes. That is, the EcoRI-HindIII fragment of pKK-brownii was exchanged with the corresponding fragment of pKK-bidentis (a plasmid obtained by inserting the cDNA of Flaveria bidentis into pKK 223-2 as in the construction of pKK-brownii) to obtain a plasmid pKK-011. On the other hand, the EcoRI-HindIII fragment of pKK-bidentis was exchanged with the corresponding fragment of pKK-brownii to obtain a plasmid pKK-100. Similarly, the NdeI-HindIII fragments were exchanged to obtain pKK-001 and pKK-110. Further, the Xho-HindIII fragment of pKK-110 was exchanged with the corresponding fragment of pKK-bidentis to obtain pKK-1101, and the XhoI-HindIII fragment of pKK-bidentis was exchanged with the corresponding fragment of pKK-brownii to obtain pKK-1110. To further finely recombine the XhoI-HindIII fragments, the fragments were linked by PCR (linking PCR method). That is, primers complementary to the nucleotide sequence in the XhoI-HindIII fragment, which sequence is common in bidentis and brownii, that is, a primer link-F: GCAGAGATGATGTTGGCAAG (SEQ ID NO. 18) and a primer link-R: CTTGCCAACAT-CATCTCTGC (SEQ ID NO. 19) were prepared. Using the XhoI-HindIII fragment of brownii or bidentis subcloned into pBluescript SK(-) as a template, and using combination of primers of link-F/RV or M4/link-R, the first PCR was carried out. The obtained fragments (totally 4 types) were purified by cutting out from the gel. Using the mixture of the fragment encoding the former half of brownii and the fragment encoding the latter half of bidentis, or the mixture of the fragment encoding the former half of bidentis and the fragment encoding the latter half of brownii as a template, and using primers M4/RV, the second PCR was performed. The amplified linked fragments were digested with XhoI and HindIII and the resultants were exchanged with the corresponding region of pKK-bidentis to obtain pKK-link01 and pKK-link10. Another pair of chimeric genes were prepared utilizing the PstI site between the recombination site in the linking PCR and the HindIII site. That is, the XhoI-PstI fragment of pKK-link10 and the PstI-HindIII fragment of pKK-bidentis were inserted into the XhoI-HindIII site of pKK-bidentis (three fragments-linking reaction) to obtain pKK-link101. Similarly, the XhoI-PstI fragment of pKK-bidentis and the PstI-HindIII fragment of pKK-brownii were inserted into the XhoI-HindIII site of pKK-bidentis to obtain pKK-link110.

The 40 sites at which the amino acid residues are different between the mature PPDK proteins of Flaveria brownii and of Flaveria bidentis are mainly exist in the N-terminal and C-terminal regions, and do not exist so many in the center region, that is, in the active site. Thus, the cDNAs were divided into three regions, that is, the front, middle and rear regions by utilizing EcoRI sites and NdeI sites which commonly exist in both of the genes, and these fragments were interchangeably exchanged to prepare chimeric genes. By checking these chimeric genes, it was determined which region is related to the cold-stability. As a result, cold-stability is acquired when the protein contains the rear ⅓ region of the cDNA of *Flaveria brownii*. In contrast, when the protein contains the rear ⅓ region of the cDNA of *Flaveria bidentis*, the protein was cold-sensitive. Then the rear ⅓ region was divided into two regions by restriction enzyme XhoI, and the fragments were respectively introduced into the corresponding regions of pKK-*bidentis* and the cold-stability was checked. As a result, the region downstream of the XhoI site (i.e., the ⅙ region from the C-terminal) was necessary and sufficient for attaining cold-stability. Then a chimeric gene containing the rear ⅙ region (XhoI-HindIII fragment, containing 7 substitutions of amino acid residues) was prepared by the linking PCR method and the amplified gene was introduced into pKK-*bidentis*, followed by measuring the cold-stability thereof. As a result, a chimeric enzyme pKK-link10 having the rear most region containing 4 substitutions was cold-stable while a chimeric enzyme pKK-link01 having the former half of the rear region, which contains 3 substitutions was cold-sensitive. Then the rear region was recombined using a restriction enzyme PstI to prepare chimeric genes having two amino acid substitutions per gene, and the cold-stability of the obtained genes was checked. As a result, all of the chimeric genes exhibited cold-stability. Thus, it is assumed that there are two or more regions related to cold-stability.

(2) Chimera of Maize and *Flaveria brownii*

Figure 3:
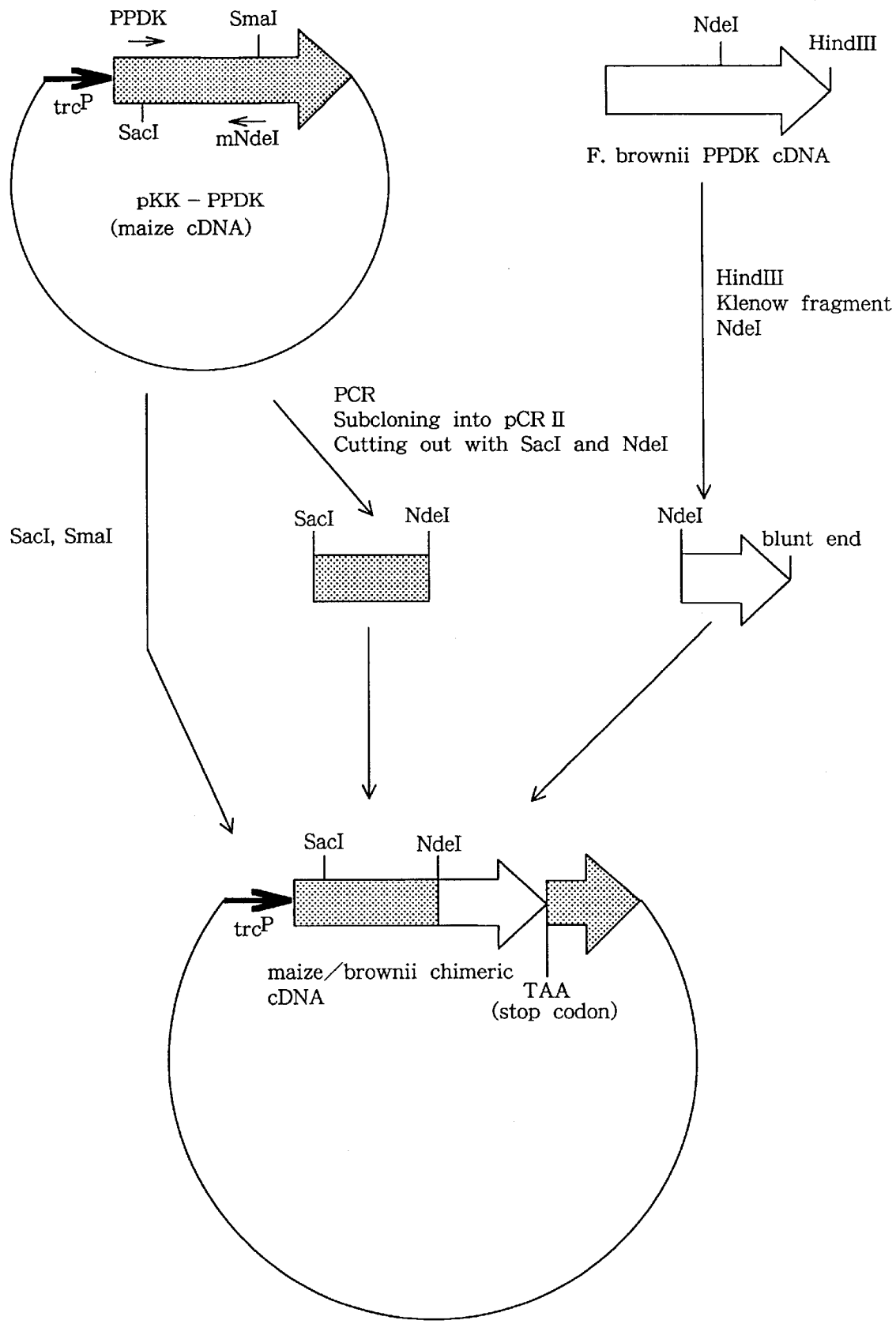
FIG. 3 schematically shows a construction method of an expression vector containing an example of the PPDK gene according to the present invention.

Using a primer PPDK-F: CTCACTGTTCGAA-GAGAAGC (SEQ ID NO. 36) and a primer mNdeI: CATAT-GCTCTGTCCGGCATAATC (SEQ ID NO. 37) (complementary chain side) containing NdeI site as primers, and cDNA of maize PPDK as a template, PCR was performed and the amplified fragment was subcloned into pCR II. This fragment was cut out from pCR II by SacI and NdeI. This fragment, the SacI-SmaI fragment (vector fragment) of pKK-PPDK and a fragment obtained by digesting cDNA of PPDK of *F. brownii*, blunting the resultant with Klenow fragment and then digesting the resultant with NdeI, were linked by three fragments-linking reaction (FIG. 3) to obtain pKK-mz/bro (Nde). PCR was performed using primer PPDK-F and a primer mXhoI: CTCGAGGGATCTCAAT-CATTG (SEQ ID NO. 21) (complementary chain), and maize PPDK as a template. The obtained fragment was subcloned into pCR II and the insert was cut out by SacI and XhoI from pCR II. The cut out fragment was ligated with the SacI-XhoI fragment (vector fragment) of pKK-mz/bro(Nde) to obtain pKK-mz/bro(Xho).

Both of the chimeric enzyme containing the C-terminal ⅓ region (NdeI-HindIII fragment) of *brownii* PPDK in maize PPDK and the chimeric enzyme containing the C-terminal ⅙ region (XhoI-HindIII fragment) of *brownii* PPDK in maize PPDK exhibited cold-stability as strong as that of *brownii*. Thus, since cold-stability could be given to maize PPDK whose amino acid sequence is considerably different from that of *F. brownii*, it is thought that cold-stability can be given to PPDKs of various plants by introducing the rear ⅓ region or the C-terminal ⅙ region. Since the thus prepared maize/*F. brownii* chimeric PPDK contains the transit peptide of maize PPDK as it is, if a transformed plant has a problem in transportation of the cold-stable PPDK to chloroplasts, in which the transit peptide is also originated from *Flaveria brownii*, this problem is thought to be overcome by introducing this chimeric gene in place of the gene originated from *F. brownii*.

(3) Point-mutated Clones

Amino acid residues of XhoI-HindIII fragment of pKK-*brownii* were changed one by one from *brownii* type to *bidentis* type. Similarly, amino acid residues of XhoI-HindIII fragment of pKK-*bidentis* were changed one by one from *bidentis* type to *brownii* type. Introduction of the mutation was carried out by subcloning the XhoI-HindIII fragments of PPDK cDNAs of *F. brownii* and of *F. bidentis* into pBluescript IISK(-), and then substituting nucleotides by Kunkel method using Megalabel kit (commercially available from TAKARA SHUZO) and Mutan-K kit (commercially available from TAKARA SHUZO). The sequence of the primers used for introducing mutations were as shown in Table 2. After confirming the mutated nucleotide sequence by a DNA sequencer, these fragments were inserted into the XhoI-HindIII site of pKK-*bidentis*.

TABLE 2

Primers Used for Preparation of Point-mutated Clones

Introduction of Mutation from *F. brownii* type to *F. bidentis* type

| | |
|---|---|
| 836DE | 5'GCAATCTCTTCAGCAATC (SEQ ID NO. 22) |
| 839AG | 5'GCTTCTTTTCCAATCTCATC (SEQ ID NO. 23) |
| 843ED | 5'CGAAAAGAAATCGGCTTC (SEQ ID NO. 24) |
| 869PQ | 5'GAAAGATAAATCTGCAAAAACTTG (SEQ ID NO. 25) |
| 873SA | 5'GCCTTGAGCAAGATAAATC (SEQ ID NO. 26) |
| 885LI | 5'TTCTGGTCAATAACCTCAATG (SEQ ID NO. 27) |
| 952VI | 5'GCTTAAACAATGACTTGTGC (SEQ ID NO. 28) |

Introduction of Mutation from *F. bidentis* type to *F. brownii* type

| | |
|---|---|
| 836ED | 5'CCAATCTCATCAGCTATTAAAG (SEQ ID NO. 29) |
| 839GA | 5'GCTTCTTTTGCAATCTCTTC (SEQ ID NO. 30) |
| 843DE | 5'CGAAAAGAACTCAGCTTC (SEQ ID NO. 31) |
| 869QP | 5'CAAGATAAATCGGCAAAAACTTG (SEQ ID NO. 32) |
| 873AS | 5'GAATGCCTTGAGAAAGATAAATC (SEQ ID NO. 33) |
| 885IL | 5'CTTTCTGGTCAAGAACCTCAAATG (SEQ ID NO. 34) |
| 952IV | 5'GCTTAAACAACGACTTGTGC (SEQ ID NO. 35) |

All of the enzymes in which one amino acid residue in the XhoI-HindIII region of pKK-1110, which amino acid residue is different between *F. brownii* and *F. bidentis*, was substituted to the corresponding amino acid residue of the *bidentis* type exhibited cold-stability. Thus, it is thought that there are a plurality of mutations which give cold-stability (because the cold-stability is not lost by changing only one amino acid residue). Then enzymes in which one amino acid residue in the XhoI-HindIII region of pKK-*bidentis*, which amino acid residue is different between *F. brownii* and *F. bidentis*, was substituted to the corresponding amino acid residue of the *brownii* type were prepared, and it was checked whether the enzymes acquired cold-stability. That is, the enzyme activity after treatment at 0° C. for 20 minutes was measured. As a result, by the mutation of 869Gln→Pro, the enzyme acquired cold-stability (the activity after the cold treatment is 60–70% of the original activity). With the mutation of 885Ile→Leu or 952Ile→Val, the loss of activity at low temperature was prevented a little. Taking these results and the results of chimeric enzyme pKK-link110 described in (1) into consideration, it is assumed that the enzyme acquires cold-stability when these mutations coexist. From these results, it was concluded that the three amino acid residues, that is, 869Pro, 885Leu and 952Val are related to cold-stability. However, among these residues relating to cold-stability of *brownii*, as for 869Pro and 885Leu, these residues are of *brownii* type in maize PPDK too. Therefore, cold-stability is not necessarily attained only by the fact that these residues are of *brownii* type, but it is thought that these residues give complete cold-stability in the amino acid sequence of PPDK of *brownii* or *bidentis*. Therefore, in cases where cold-stability is to be given to a PPDK originated from a different species, whose amino acid sequence is considerably different from those of *brownii* and *bidentis*, it is preferred not to introduce point mutations, but to prepare a chimeric gene in which a region giving cold-stability is introduced as carried out for maize PPDK.

4. Transformation of Maize with PPDK Gene of *Flaveria brownii*

In accordance with the method of Gordon-Kamm W. J. et al (The Plant Cell 2:603–618, 1990) or Koziel M. G. et al.(Bio/Technology 11:194–200, 1993), gold or tungsten fine particles are coated with pKK-*brownii*, and the coated particles are implanted into maize immature embryos or suspended cultured cells. From the treated cells, transformants are selected, and obtained calli of transformants are cultured according to a conventional method, followed by regenerating plants from the calli. The method of transformation is not restricted to the particle gun method, but the methods of transformation which may be employed include electroporation method (Rhodes C. A. et al., Science 240:204–207, 1988), PEG method (Armstrong C. L. et al., Plant Cell Reports 9:335–339, 1990), tissue-electroporation method (D'Halluin K. et al., The Plant Cell 4:1495–1505, 1992), Agrobacterium method (Hiei Y. and Komari T. WO 9400977) and the like. From the obtained plants, seeds are recovered and germinated to regenerate plants. PPDK is isolated from leaves of the obtained plants and its cold-stability is checked. For transformed plants and non-transformed plants, effect of temperature with respect to photosynthesis rate is checked. Stability of the transformation is assured by proliferating maize plants which exhibit high photosynthesis rates at low temperature for many generations, and measuring the photosynthesis rates at different temperatures and measuring the cold-stability of PPDKs isolated from the plants.

5. Transformation of *Flaveria bidentis* with PPDK gene of *Flaveria brownii*

An intermediate vector containing the full-length cDNA shown in SEQ ID NOS. 9 and 10) and a reporter gene is introduced into a disarmed Ti plasmid of *Agrobacterium tumefaciens*. This can be accomplished by the method described in Draper J et al. eds., Plant Genetic Transformation and Gene Expression—a laboratory manual, Blackwell Scientific Publications (ISBN 0-632-02172-1).

On the other hand, leaf tissue or callus of *Flaveria bidentis* is infected with the above-mentioned *Agrobacterium tumefaciens*. This can be accomplished by culturing the tissue or callus together with *Agrobacterium tumefaciens*. Infected cells are selected based on the drug resistance. From the selected calli, whole plants are generated by a conventional methods. From the obtained plants, seeds are recovered and germinated to regenerate plants. PPDK is isolated from leaves of the obtained plants and its cold-stability is checked. For transformed plants and non-transformed plants, effect of temperature with respect to photosynthesis rate is checked. Stability of the transformation is assured by proliferating maize plants which exhibit high photosynthesis rates at low temperature for many generations, and measuring the photosynthesis rates at different temperatures and measuring the cold-stability of PPDKs isolated from the plants.

We claim:

1. A chimeric pyruvate, orthophosphate dikinase polypeptide wherein a region of the amino acid sequence of the pyruvate, orthophosphate dikinase, corresponding to the amino acid sequence of the 832nd to 955th amino acid residues of SEQ ID NO:10, is substituted with the amino acid sequence of the 832nd to 955th amino acid residue of the amino acid sequence shown in SEQ ID NO:10, giving cold stability to the chimeric polypeptide having pyruvate, orthophosphate dikinase activity.

2. A polypeptide comprising the amino acid sequence of SEQ ID NO:2 except that the 869th amino acid residue is proline.

3. A polypeptide comprising the amino acid sequence of SEQ ID NO:2 except that the 885th and 952nd amino acid residues are leucine and valine, respectively.

4. A cloned DNA encoding the polypeptide of SEQ ID NO:10 or encoding the polypeptide according to any one of claims 1 to 3.

5. The DNA according to claim 4, comprising the nucleotide sequence SEQ ID NO:9 or comprising the nucleotide sequence of SEQ ID NO:9 and encoding polypeptide having cold-stable pyruvate, orthophosphate dikinase activity.

6. A recombinant vector containing said DNA according to claim 4, which expresses in a host, a polypeptide having cold-stable pyruvate, orthophosphate dikinase activity.

7. A plant transformed with the DNA according to claim 4.

8. A method for producing a polypeptide having cold-stable pyruvate, orthophosphate dikinase activity, comprising the step of substituting the region of the amino acid sequence of a pyravate, orthophosphate dikinase, corresponding to the amino acid sequence of the 832nd to 955th amino acid residues of SEQ ID NO:10, with the amino acid sequence of the 832nd to 955th amino acid residues of SEQ ID NO:10.

* * * * *

SEQUENCE LISTING (1) GENERAL INFORMATION:

(iii) NUMBER OF SEQUENCES: 37

(2) INFORMATION FOR SEQ ID NO:1:

(i) SEQUENCE CHARACTERISTICS:
      (A) LENGTH: 2915 base pairs
      (B) TYPE: nucleic acid
      (C) STRANDEDNESS: single
      (D) TOPOLOGY: linear (ii) MOLECULE TYPE: other nucleic acid (ix) FEATURE:
      (A) NAME/KEY: CDS
      (B) LOCATION: 50..2908

(xi) SEQUENCE DESCRIPTION: SEQ ID NO:1:

```
CGATCTCCTT CTGCTATTGC TGATATCTCA ATTTCACAGG TGAAGAAGG ATG ATG           55
                                                     Met Met
                                                       1

AGT TCG TTG TCT GTT GAA GGT ATG CTT CTC AAG TCA GCC CGT GAG TCG        103
Ser Ser Leu Ser Val Glu Gly Met Leu Leu Lys Ser Ala Arg Glu Ser
          5                  10                  15

TGC TTA CCG GCG AGA GTG AAG CAA CGG CGA AAC GGT GAT CTC CGG CGA        151
Cys Leu Pro Ala Arg Val Lys Gln Arg Arg Asn Gly Asp Leu Arg Arg
     20                  25                  30

TTG AAC CAC CAC CGT CAA TCG TCG TTT GTC CGG TGT TTA ACT CCG GCG        199
Leu Asn His His Arg Gln Ser Ser Phe Val Arg Cys Leu Thr Pro Ala
 35                  40                  45                  50

AGA GTT AGC AGA CCA GAG TTG CGC AGC AGT GGC TTA ACT CCG CCG CGA        247
Arg Val Ser Arg Pro Glu Leu Arg Ser Ser Gly Leu Thr Pro Pro Arg
              55                  60                  65
```

```
GCA GTT CTT AAT CCG GTG TCT CCT CCG GTG ACG ACG GCT AAA AAG AGG      295
Ala Val Leu Asn Pro Val Ser Pro Pro Val Thr Thr Ala Lys Lys Arg
            70              75              80

GTT TTC ACT TTT GGT AAA GGA AGA AGT GAA GGC AAC AGG GAC ATG AAA      343
Val Phe Thr Phe Gly Lys Gly Arg Ser Glu Gly Asn Arg Asp Met Lys
            85              90              95

TCC TTG TTG GGA GGA AAA GGA GCA AAT CTT GCT GAG ATG TCA AGC ATT      391
Ser Leu Leu Gly Gly Lys Gly Ala Asn Leu Ala Glu Met Ser Ser Ile
100             105             110

GGT CTA TCA GTT CCT CCT GGG CTC ACT ATT TCA ACT GAA GCA TGT GAG      439
Gly Leu Ser Val Pro Pro Gly Leu Thr Ile Ser Thr Glu Ala Cys Glu
115             120             125             130

GAA TAT CAA CAA AAT GGA AAG AGC CTA CCT CCA GGT TTG TGG GAT GAG      487
Glu Tyr Gln Gln Asn Gly Lys Ser Leu Pro Pro Gly Leu Trp Asp Glu
            135             140             145

ATT TCA GAA GGC TTA GAT TAT GTC CAG AAA GAG ATG TCT GCA TCT CTC      535
Ile Ser Glu Gly Leu Asp Tyr Val Gln Lys Glu Met Ser Ala Ser Leu
            150             155             160

GGT GAC CCG TCT AAA CCT CTC CTC CTT TCC GTC CGT TCG GGT GCT GCC      583
Gly Asp Pro Ser Lys Pro Leu Leu Leu Ser Val Arg Ser Gly Ala Ala
            165             170             175

ATA TCT ATG CCT GGT ATG ATG GAC ACT GTA TTG AAT CTC GGG CTT AAT      631
Ile Ser Met Pro Gly Met Met Asp Thr Val Leu Asn Leu Gly Leu Asn
180             185             190

GAT GAG GTC GTA GCT GGT CTA GCT GGC AAA AGT GGA GCA CGG TTT GCC      679
Asp Glu Val Val Ala Gly Leu Ala Gly Lys Ser Gly Ala Arg Phe Ala
195             200             205             210

TAT GAC TCG TAT AGA AGG TTT CTC GAT ATG TTT GGC AAC GTT GTA ATG      727
Tyr Asp Ser Tyr Arg Arg Phe Leu Asp Met Phe Gly Asn Val Val Met
            215             220             225

GGT ATC CCG CAT TCA TTA TTT GAC GAA AAG TTA GAG CAG ATG AAA GCT      775
Gly Ile Pro His Ser Leu Phe Asp Glu Lys Leu Glu Gln Met Lys Ala
            230             235             240

GAA AAA GGG ATT CAT CTC GAC ACC GAT CTC ACT GCT GCT GAT CTT AAA      823
Glu Lys Gly Ile His Leu Asp Thr Asp Leu Thr Ala Ala Asp Leu Lys
            245             250             255

GAT CTT GTT GAG AAA TAC AAG AAC GTG TAT GTG GAA GCA AAG GGC GAA      871
Asp Leu Val Glu Lys Tyr Lys Asn Val Tyr Val Glu Ala Lys Gly Glu
260             265             270

AAG TTT CCC ACA GAT CCA AAG AAA CAG CTA GAG TTA GCA GTG AAT GCT      919
Lys Phe Pro Thr Asp Pro Lys Lys Gln Leu Glu Leu Ala Val Asn Ala
275             280             285             290

GTT TTT GAT TCT TGG GAC AGC CCA AGG GCC AAT AAG TAC AGA AGT ATT      967
Val Phe Asp Ser Trp Asp Ser Pro Arg Ala Asn Lys Tyr Arg Ser Ile
            295             300             305

AAC CAG ATA ACT GGA TTA AAG GGG ACT GCA GTT AAC ATT CAA AGC ATG     1015
Asn Gln Ile Thr Gly Leu Lys Gly Thr Ala Val Asn Ile Gln Ser Met
            310             315             320

GTG TTT GGC AAC ATG GGA AAC ACT TCA GGA ACT GGT GTT CTT TTC ACT     1063
Val Phe Gly Asn Met Gly Asn Thr Ser Gly Thr Gly Val Leu Phe Thr
            325             330             335

AGG AAC CCA AGC ACC GGT GAG AAG AAG CTA TAC GGG GAG TTT TTA ATC     1111
Arg Asn Pro Ser Thr Gly Glu Lys Lys Leu Tyr Gly Glu Phe Leu Ile
            340             345             350

AAT GCT CAG GGA GAG GAT GTT GTT GCT GGG ATC AGA ACA CCA GAA GAT     1159
Asn Ala Gln Gly Glu Asp Val Val Ala Gly Ile Arg Thr Pro Glu Asp
355             360             365             370

TTG GGG ACC ATG GAG ACT TGC ATG CCT GAT GCA TAC AAA GAG CTT GTG     1207
Leu Gly Thr Met Glu Thr Cys Met Pro Asp Ala Tyr Lys Glu Leu Val
            375             380             385
```

```
GAG AAC TGC GAG ATC TTA GAG GGA CAC TAC AAA GAT ATG ATG GAT ATT    1255
Glu Asn Cys Glu Ile Leu Glu Gly His Tyr Lys Asp Met Met Asp Ile
            390                 395                 400

GAA TTC ACA GTT CAA GAA AAC AGG CTT TGG ATG TTG CAA TGC CGA ACA    1303
Glu Phe Thr Val Gln Glu Asn Arg Leu Trp Met Leu Gln Cys Arg Thr
        405                 410                 415

GGG AAA CGT ACT GGT AAA GGT GCA GTG AGA ATT GCA GTA GAT ATG GTG    1351
Gly Lys Arg Thr Gly Lys Gly Ala Val Arg Ile Ala Val Asp Met Val
    420                 425                 430

AAC GAA GGG CTA ATT GAT ACT AGA ACA GCA ATT AAG AGG GTT GAG ACT    1399
Asn Glu Gly Leu Ile Asp Thr Arg Thr Ala Ile Lys Arg Val Glu Thr
435                 440                 445                 450

CAA CAT CTA GAT CAG CTT CTT CAT CCA CAG TTT GAG GAT CCG TCT GCT    1447
Gln His Leu Asp Gln Leu Leu His Pro Gln Phe Glu Asp Pro Ser Ala
                455                 460                 465

TAC AAA AGC CAT GTG GTA GCA ACC GGT TTG CCA GCA TCC CCC GGG GCA    1495
Tyr Lys Ser His Val Val Ala Thr Gly Leu Pro Ala Ser Pro Gly Ala
            470                 475                 480

GCT GTG GGA CAG GTT TGT TTT AGT GCA GAG GAT GCA GAA ACA TGG CAT    1543
Ala Val Gly Gln Val Cys Phe Ser Ala Glu Asp Ala Glu Thr Trp His
        485                 490                 495

GCA CAA GGA AAG AGT GCT ATC TTG GTA AGG ACC GAA ACA AGC CCA GAA    1591
Ala Gln Gly Lys Ser Ala Ile Leu Val Arg Thr Glu Thr Ser Pro Glu
    500                 505                 510

GAT GTT GGT GGT ATG CAT GCA GCA GCT GGA ATC TTA ACC GCT AGA GGA    1639
Asp Val Gly Gly Met His Ala Ala Ala Gly Ile Leu Thr Ala Arg Gly
515                 520                 525                 530

GGC ATG ACA TCA CAT GCA GCG GTG GTG GCT CGC GGA TGG GGC AAA TGT    1687
Gly Met Thr Ser His Ala Ala Val Val Ala Arg Gly Trp Gly Lys Cys
                535                 540                 545

TGT GTT TCC GGT TGT GCT GAT ATT CGT GTG AAC GAT GAT ATG AAG ATT    1735
Cys Val Ser Gly Cys Ala Asp Ile Arg Val Asn Asp Asp Met Lys Ile
            550                 555                 560

TTT ACG ATT GGC GAC CGT GTG ATT AAA GAA GGC GAC TGG CTT TCT CTT    1783
Phe Thr Ile Gly Asp Arg Val Ile Lys Glu Gly Asp Trp Leu Ser Leu
        565                 570                 575

AAT GGT ACA ACT GGT GAA GTC ATA TTG GGT AAA CAG CTA CTG GCT CCA    1831
Asn Gly Thr Thr Gly Glu Val Ile Leu Gly Lys Gln Leu Leu Ala Pro
    580                 585                 590

CCT GCA ATG AGC AAT GAC TTA GAA ATA TTC ATG TCA TGG GCT GAT CAA    1879
Pro Ala Met Ser Asn Asp Leu Glu Ile Phe Met Ser Trp Ala Asp Gln
595                 600                 605                 610

GCA AGG CGT CTC AAG GTT ATG GCA AAT GCA GAC ACA CCT AAT GAT GCA    1927
Ala Arg Arg Leu Lys Val Met Ala Asn Ala Asp Thr Pro Asn Asp Ala
                615                 620                 625

TTA ACA GCC AGA AAC AAT GGT GCA CAA GGG ATC GGG CTC TGT AGA ACT    1975
Leu Thr Ala Arg Asn Asn Gly Ala Gln Gly Ile Gly Leu Cys Arg Thr
            630                 635                 640

GAA CAT ATG TTT TTC GCT TCT GAT GAG AGG ATC AAA GCT GTA AGA AAG    2023
Glu His Met Phe Phe Ala Ser Asp Glu Arg Ile Lys Ala Val Arg Lys
        645                 650                 655

ATG ATC ATG GCG GTC ACT CCA GAA CAA AGA AAA GTG GCT CTA GAT CTC    2071
Met Ile Met Ala Val Thr Pro Glu Gln Arg Lys Val Ala Leu Asp Leu
    660                 665                 670

TTA CTC CCA TAC CAA AGA TCC GAT TTT GAG GGC ATT TTC CGA GCA ATG    2119
Leu Leu Pro Tyr Gln Arg Ser Asp Phe Glu Gly Ile Phe Arg Ala Met
675                 680                 685                 690

GAT GGA CTT CCT GTA ACT ATC CGC CTT CTA GAC CCT CCA CTT CAT GAG    2167
Asp Gly Leu Pro Val Thr Ile Arg Leu Leu Asp Pro Pro Leu His Glu
                695                 700                 705
```

```
TTT TTA CCC GAA GGT GAT CTA GAA CAC ATA GTG AAC GAA CTT GCA GTC        2215
Phe Leu Pro Glu Gly Asp Leu Glu His Ile Val Asn Glu Leu Ala Val
            710                 715                 720

GAC ACA GGC ATG AGT GCA GAT GAA ATC TAT TCA AAA ATC GAA AAT CTA        2263
Asp Thr Gly Met Ser Ala Asp Glu Ile Tyr Ser Lys Ile Glu Asn Leu
            725                 730                 735

TCT GAA GTG AAC CCT ATG CTT GGT TTC CGT GGT TGC AGA TTA GGG ATT        2311
Ser Glu Val Asn Pro Met Leu Gly Phe Arg Gly Cys Arg Leu Gly Ile
        740                 745                 750

TCA TAC CCC GAG CTA ACA GAA ATG CAA GTT CGT GCG ATC TTT CAA GCT        2359
Ser Tyr Pro Glu Leu Thr Glu Met Gln Val Arg Ala Ile Phe Gln Ala
755                 760                 765                 770

GCA GTG TCT ATG ACC AAT CAG GGG GTG ACT GTA ATA CCA GAG ATC ATG        2407
Ala Val Ser Met Thr Asn Gln Gly Val Thr Val Ile Pro Glu Ile Met
                775                 780                 785

GTT CCG TTA GTG GGG ACA CCT CAG GAA TTA CGT CAT CAA ATC AGT GTA        2455
Val Pro Leu Val Gly Thr Pro Gln Glu Leu Arg His Gln Ile Ser Val
            790                 795                 800

ATT CGT GGA GTA GCT GCA AAT GTG TTT GCT GAA ATG GGG GTG ACA TTG        2503
Ile Arg Gly Val Ala Ala Asn Val Phe Ala Glu Met Gly Val Thr Leu
        805                 810                 815

GAA TAT AAA GTG GGA ACG ATG ATT GAG ATT CCT CGA GCT GCT TTA ATA        2551
Glu Tyr Lys Val Gly Thr Met Ile Glu Ile Pro Arg Ala Ala Leu Ile
820                 825                 830

GCT GAA GAG ATT GGA AAA GAA GCT GAT TTC TTT TCG TTT GGA ACC AAT        2599
Ala Glu Glu Ile Gly Lys Glu Ala Asp Phe Phe Ser Phe Gly Thr Asn
835                 840                 845                 850

GAT CTG ACC CAG ATG ACA TTT GGG TAC AGC AGA GAT GAT GTT GGC AAG        2647
Asp Leu Thr Gln Met Thr Phe Gly Tyr Ser Arg Asp Asp Val Gly Lys
                855                 860                 865

TTT TTG CAG ATT TAT CTT GCT CAA GGC ATT CTG CAG CAT GAT CCA TTT        2695
Phe Leu Gln Ile Tyr Leu Ala Gln Gly Ile Leu Gln His Asp Pro Phe
            870                 875                 880

GAG GTT ATT GAC CAG AAA GGG GTG GGT CAG TTG ATT AAG ATG GCT ACG        2743
Glu Val Ile Asp Gln Lys Gly Val Gly Gln Leu Ile Lys Met Ala Thr
        885                 890                 895

GAG AAA GGT CGT GCA GCA AAT CCT AAC TTA AAG GTT GGG ATA TGT GGG        2791
Glu Lys Gly Arg Ala Ala Asn Pro Asn Leu Lys Val Gly Ile Cys Gly
900                 905                 910

GAG CAT GGT GGG GAG CCT TCT TCT GTT GCA TTT TTT GAT GGA GTT GGA        2839
Glu His Gly Gly Glu Pro Ser Ser Val Ala Phe Phe Asp Gly Val Gly
915                 920                 925                 930

CTA GAT TAT GTG TCG TGC TCT CCA TTT AGG GTT CCT ATC GCA AGG TTG        2887
Leu Asp Tyr Val Ser Cys Ser Pro Phe Arg Val Pro Ile Ala Arg Leu
                935                 940                 945

GCC GCT GCA CAA GTC ATT GTT TAAGCTT                                     2915
Ala Ala Ala Gln Val Ile Val
            950

(2) INFORMATION FOR SEQ ID NO:2:

(i) SEQUENCE CHARACTERISTICS:
        (A) LENGTH: 953 amino acids
        (B) TYPE: amino acid
        (D) TOPOLOGY: linear (ii) MOLECULE TYPE: protein (xi) SEQUENCE DESCRIPTION: SEQ ID NO:2:

Met Met Ser Ser Leu Ser Val Glu Gly Met Leu Leu Lys Ser Ala Arg
1               5                   10                  15
```

-continued

```
Glu Ser Cys Leu Pro Ala Arg Val Lys Gln Arg Arg Asn Gly Asp Leu
         20                  25                  30

Arg Arg Leu Asn His His Arg Gln Ser Ser Phe Val Arg Cys Leu Thr
         35                  40                  45

Pro Ala Arg Val Ser Arg Pro Glu Leu Arg Ser Ser Gly Leu Thr Pro
 50                  55                  60

Pro Arg Ala Val Leu Asn Pro Val Ser Pro Val Thr Thr Ala Lys
 65                  70                  75                  80

Lys Arg Val Phe Thr Phe Gly Lys Gly Arg Ser Glu Gly Asn Arg Asp
                 85                  90                  95

Met Lys Ser Leu Leu Gly Gly Lys Gly Ala Asn Leu Ala Glu Met Ser
                100                 105                 110

Ser Ile Gly Leu Ser Val Pro Pro Gly Leu Thr Ile Ser Thr Glu Ala
                115                 120                 125

Cys Glu Glu Tyr Gln Gln Asn Gly Lys Ser Leu Pro Pro Gly Leu Trp
130                 135                 140

Asp Glu Ile Ser Glu Gly Leu Asp Tyr Val Gln Lys Glu Met Ser Ala
145                 150                 155                 160

Ser Leu Gly Asp Pro Ser Lys Pro Leu Leu Leu Ser Val Arg Ser Gly
                165                 170                 175

Ala Ala Ile Ser Met Pro Gly Met Met Asp Thr Val Leu Asn Leu Gly
                180                 185                 190

Leu Asn Asp Glu Val Val Ala Gly Leu Ala Gly Lys Ser Gly Ala Arg
                195                 200                 205

Phe Ala Tyr Asp Ser Tyr Arg Arg Phe Leu Asp Met Phe Gly Asn Val
210                 215                 220

Val Met Gly Ile Pro His Ser Leu Phe Asp Glu Lys Leu Glu Gln Met
225                 230                 235                 240

Lys Ala Glu Lys Gly Ile His Leu Asp Thr Asp Leu Thr Ala Ala Asp
                245                 250                 255

Leu Lys Asp Leu Val Glu Lys Tyr Lys Asn Val Tyr Val Glu Ala Lys
                260                 265                 270

Gly Glu Lys Phe Pro Thr Asp Pro Lys Lys Gln Leu Glu Leu Ala Val
                275                 280                 285

Asn Ala Val Phe Asp Ser Trp Asp Ser Pro Arg Ala Asn Lys Tyr Arg
290                 295                 300

Ser Ile Asn Gln Ile Thr Gly Leu Lys Gly Thr Ala Val Asn Ile Gln
305                 310                 315                 320

Ser Met Val Phe Gly Asn Met Gly Asn Thr Ser Gly Thr Gly Val Leu
                325                 330                 335

Phe Thr Arg Asn Pro Ser Thr Gly Glu Lys Lys Leu Tyr Gly Glu Phe
                340                 345                 350

Leu Ile Asn Ala Gln Gly Glu Asp Val Val Ala Gly Ile Arg Thr Pro
                355                 360                 365

Glu Asp Leu Gly Thr Met Glu Thr Cys Met Pro Asp Ala Tyr Lys Glu
 370                 375                 380

Leu Val Glu Asn Cys Glu Ile Leu Glu Gly His Tyr Lys Asp Met Met
385                 390                 395                 400

Asp Ile Glu Phe Thr Val Gln Glu Asn Arg Leu Trp Met Leu Gln Cys
                405                 410                 415

Arg Thr Gly Lys Arg Thr Gly Lys Gly Ala Val Arg Ile Ala Val Asp
                420                 425                 430

Met Val Asn Glu Gly Leu Ile Asp Thr Arg Thr Ala Ile Lys Arg Val
                435                 440                 445
```

-continued

```
Glu Thr Gln His Leu Asp Gln Leu Leu His Pro Gln Phe Glu Asp Pro
    450                 455                 460

Ser Ala Tyr Lys Ser His Val Val Ala Thr Gly Leu Pro Ala Ser Pro
465                 470                 475                 480

Gly Ala Ala Val Gly Gln Val Cys Phe Ser Ala Glu Asp Ala Glu Thr
                485                 490                 495

Trp His Ala Gln Gly Lys Ser Ala Ile Leu Val Arg Thr Glu Thr Ser
                500                 505                 510

Pro Glu Asp Val Gly Gly Met His Ala Ala Gly Ile Leu Thr Ala
            515                 520                 525

Arg Gly Gly Met Thr Ser His Ala Ala Val Val Ala Arg Gly Trp Gly
    530                 535                 540

Lys Cys Cys Val Ser Gly Cys Ala Asp Ile Arg Val Asn Asp Asp Met
545                 550                 555                 560

Lys Ile Phe Thr Ile Gly Asp Arg Val Ile Lys Glu Gly Asp Trp Leu
                565                 570                 575

Ser Leu Asn Gly Thr Thr Gly Glu Val Ile Leu Gly Lys Gln Leu Leu
                580                 585                 590

Ala Pro Pro Ala Met Ser Asn Asp Leu Glu Ile Phe Met Ser Trp Ala
    595                 600                 605

Asp Gln Ala Arg Arg Leu Lys Val Met Ala Asn Ala Asp Thr Pro Asn
    610                 615                 620

Asp Ala Leu Thr Ala Arg Asn Asn Gly Ala Gln Gly Ile Gly Leu Cys
625                 630                 635                 640

Arg Thr Glu His Met Phe Phe Ala Ser Asp Glu Arg Ile Lys Ala Val
                645                 650                 655

Arg Lys Met Ile Met Ala Val Thr Pro Glu Gln Arg Lys Val Ala Leu
                660                 665                 670

Asp Leu Leu Leu Pro Tyr Gln Arg Ser Asp Phe Glu Gly Ile Phe Arg
                675                 680                 685

Ala Met Asp Gly Leu Pro Val Thr Ile Arg Leu Leu Asp Pro Pro Leu
    690                 695                 700

His Glu Phe Leu Pro Glu Gly Asp Leu Glu His Ile Val Asn Glu Leu
705                 710                 715                 720

Ala Val Asp Thr Gly Met Ser Ala Asp Glu Ile Tyr Ser Lys Ile Glu
                725                 730                 735

Asn Leu Ser Glu Val Asn Pro Met Leu Gly Phe Arg Gly Cys Arg Leu
                740                 745                 750

Gly Ile Ser Tyr Pro Glu Leu Thr Glu Met Gln Val Arg Ala Ile Phe
            755                 760                 765

Gln Ala Ala Val Ser Met Thr Asn Gln Gly Val Thr Val Ile Pro Glu
    770                 775                 780

Ile Met Val Pro Leu Val Gly Thr Pro Gln Glu Leu Arg His Gln Ile
785                 790                 795                 800

Ser Val Ile Arg Gly Val Ala Ala Asn Val Phe Ala Glu Met Gly Val
                805                 810                 815

Thr Leu Glu Tyr Lys Val Gly Thr Met Ile Glu Ile Pro Arg Ala Ala
                820                 825                 830

Leu Ile Ala Glu Glu Ile Gly Lys Glu Ala Asp Phe Ser Phe Gly
    835                 840                 845

Thr Asn Asp Leu Thr Gln Met Thr Phe Gly Tyr Ser Arg Asp Asp Val
    850                 855                 860

Gly Lys Phe Leu Gln Ile Tyr Leu Ala Gln Gly Ile Leu Gln His Asp
```

```
                     865                 870                 875                 880

Pro Phe Glu Val Ile Asp Gln Lys Gly Val Gly Gln Leu Ile Lys Met
                                    885                 890                 895

Ala Thr Glu Lys Gly Arg Ala Ala Asn Pro Asn Leu Lys Val Gly Ile
                                900                 905                 910

Cys Gly Glu His Gly Gly Glu Pro Ser Ser Val Ala Phe Phe Asp Gly
                                915                 920                 925

Val Gly Leu Asp Tyr Val Ser Cys Ser Pro Phe Arg Val Pro Ile Ala
                                930                 935                 940

Arg Leu Ala Ala Ala Gln Val Ile Val
                945                 950

(2) INFORMATION FOR SEQ ID NO:3:

(i) SEQUENCE CHARACTERISTICS:
          (A) LENGTH: 2880 base pairs
          (B) TYPE: nucleic acid
          (C) STRANDEDNESS: single
          (D) TOPOLOGY: linear (ii) MOLECULE TYPE: other nucleic acid (ix) FEATURE:
          (A) NAME/KEY: CDS
          (B) LOCATION: 24..2864

(xi) SEQUENCE DESCRIPTION: SEQ ID NO:3:

CGGCGCAGTA GGGGATCGGA AGG ATG GCG GCA TCG GTT TCC AGG GCC ATC              50
                         Met Ala Ala Ser Val Ser Arg Ala Ile
                           1               5

TGC GTA CAG AAG CCG GGC TCA AAA TGC ACC AGG GAC AGG GAA GCG ACC            98
Cys Val Gln Lys Pro Gly Ser Lys Cys Thr Arg Asp Arg Glu Ala Thr
 10              15                  20                  25

TCC TTC GCC CGC CGA TCG GTC GCA GCG CCG AGG CCC CCG CAC GCC AAA           146
Ser Phe Ala Arg Arg Ser Val Ala Ala Pro Arg Pro Pro His Ala Lys
                 30                  35                  40

GCC CGC CGG CGT CAT CCG CTC CGA CTC CGG CGC GGG ACG GGG CCA CAT           194
Ala Arg Arg Arg His Pro Leu Arg Leu Arg Arg Gly Thr Gly Pro His
             45                  50                  55

TGC TCG CCG CTG AGG GCC GTC GTT GAC GCC GCG CCG ATA CAG ACG ACC           242
Cys Ser Pro Leu Arg Ala Val Val Asp Ala Ala Pro Ile Gln Thr Thr
         60                  65                  70

AAA AAG AGG GTG TTC CAC TTC GGC AAG GGC AAG AGC GAG GGC AAC AAG           290
Lys Lys Arg Val Phe His Phe Gly Lys Gly Lys Ser Glu Gly Asn Lys
 75                  80                  85

ACC ATG AAG GAA CTG CTG GGC GGC AAG GGC GCG AAC CTG GCG GAG ATG           338
Thr Met Lys Glu Leu Leu Gly Gly Lys Gly Ala Asn Leu Ala Glu Met
 90                  95                 100                 105

GCG AGC ATC GGG CTG TCG GTG CCG CCA GGG TTC ACG GTG TCG ACG GAG           386
Ala Ser Ile Gly Leu Ser Val Pro Pro Gly Phe Thr Val Ser Thr Glu
                110                 115                 120

GCG TGC CAG CAG TAC CAG GAC GCC GGG TGC GCC CTC CCC GCG GGG CTC           434
Ala Cys Gln Gln Tyr Gln Asp Ala Gly Cys Ala Leu Pro Ala Gly Leu
            125                 130                 135

TGG GCC GAG ATC GTC GAC GGC CTG CAG TGG GTG GAG GAG TAC ATG GGC           482
Trp Ala Glu Ile Val Asp Gly Leu Gln Trp Val Glu Glu Tyr Met Gly
        140                 145                 150

GCC ACC CTG GGC GAT CCG CAG CGC CCG CTC CTG CTC TCC GTC CGC TCC           530
Ala Thr Leu Gly Asp Pro Gln Arg Pro Leu Leu Leu Ser Val Arg Ser
        155                 160                 165

GGC GCC GCC GTG TCC ATG CCC GGC ATG ATG GAC ACG GTG CTC AAC CTG           578
Gly Ala Ala Val Ser Met Pro Gly Met Met Asp Thr Val Leu Asn Leu
```

```
                170                 175                 180                 185
GGG CTC AAC GAC GAA GTG GCC GCC GGG CTG GCG GCC AAG AGC GGG GAG        626
Gly Leu Asn Asp Glu Val Ala Ala Gly Leu Ala Ala Lys Ser Gly Glu
                190                 195                 200

CGC TTC GCC TAC GAC TCC TTC CGC CGC TTC CTC GAC ATG TTC GGC AAC        674
Arg Phe Ala Tyr Asp Ser Phe Arg Arg Phe Leu Asp Met Phe Gly Asn
                    205                 210                 215

GTC GTC ATG GAC ATC CCC CGC TCA CTG TTC GAA GAG AAG CTT GAG CAC        722
Val Val Met Asp Ile Pro Arg Ser Leu Phe Glu Glu Lys Leu Glu His
            220                 225                 230

ATG AAG GAA TCC AAG GGG CTG AAG AAC GAC ACC GAC CTC ACG GCC TCT        770
Met Lys Glu Ser Lys Gly Leu Lys Asn Asp Thr Asp Leu Thr Ala Ser
        235                 240                 245

GAC CTC AAA GAG CTC GTG GGT CAG TAC AAG GAG GTC TAC CTC TCA GCC        818
Asp Leu Lys Glu Leu Val Gly Gln Tyr Lys Glu Val Tyr Leu Ser Ala
250                 255                 260                 265

AAG GGA GAG CCA TTC CCC TCA GAC CCC AAG AAG CAG CTG GAG CTA GCA        866
Lys Gly Glu Pro Phe Pro Ser Asp Pro Lys Lys Gln Leu Glu Leu Ala
                270                 275                 280

GTG CTG GCT GTG TTC AAC TCG TGG GAG AGC CCC AGG GCC AAG AAG TAC        914
Val Leu Ala Val Phe Asn Ser Trp Glu Ser Pro Arg Ala Lys Lys Tyr
                    285                 290                 295

AGG AGC ATC AAC CAG ATC ACT GGC CTC AGG GGC ACC GCC GTG AAC GTG        962
Arg Ser Ile Asn Gln Ile Thr Gly Leu Arg Gly Thr Ala Val Asn Val
                300                 305                 310

CAG TGC ATG GTG TTC GGC AAC ATG GGG AAC ACT TCT GGC ACC GGC GTG       1010
Gln Cys Met Val Phe Gly Asn Met Gly Asn Thr Ser Gly Thr Gly Val
        315                 320                 325

CTC TTC ACC AGG AAC CCC AAC ACC GGA GAG AAG AAG CTG TAT GGC GAG       1058
Leu Phe Thr Arg Asn Pro Asn Thr Gly Glu Lys Lys Leu Tyr Gly Glu
330                 335                 340                 345

TTC CTG GTG AAC GCT CAG GGT GAG GAT GTG GTT GCC GGA ATA AGA ACC       1106
Phe Leu Val Asn Ala Gln Gly Glu Asp Val Val Ala Gly Ile Arg Thr
                350                 355                 360

CCA GAG GAC CTT GAC GCC ATG AAG AAC CTC ATG CCA CAG GCC TAC GAC       1154
Pro Glu Asp Leu Asp Ala Met Lys Asn Leu Met Pro Gln Ala Tyr Asp
                    365                 370                 375

GAG CTT GTT GAG AAC TGC AAC ATC CTG GAG AGC CAC TAC AAG GAA ATG       1202
Glu Leu Val Glu Asn Cys Asn Ile Leu Glu Ser His Tyr Lys Glu Met
            380                 385                 390

CAG GAT ATC GAG TTC ACT GTC CAG GAA AAC AGG CTG TGG ATG TTG CAG       1250
Gln Asp Ile Glu Phe Thr Val Gln Glu Asn Arg Leu Trp Met Leu Gln
        395                 400                 405

TGC AGG ACA GGG AAA CGT ACG GGC AAA AGT GCC GTG AAG ATC GCC GTG       1298
Cys Arg Thr Gly Lys Arg Thr Gly Lys Ser Ala Val Lys Ile Ala Val
410                 415                 420                 425

GAC ATG GTT AAC GAG GGC CTT GTT GAG CCC CGC TCA GCG ATC AAG ATG       1346
Asp Met Val Asn Glu Gly Leu Val Glu Pro Arg Ser Ala Ile Lys Met
                430                 435                 440

GTA GAG CCA GGC CAC CTG GAC CAG CTT CTT CAT CCT CAG TTT GAG AAC       1394
Val Glu Pro Gly His Leu Asp Gln Leu Leu His Pro Gln Phe Glu Asn
                    445                 450                 455

CCG TCG GCG TAC AAG GAT CAA GTC ATT GCC ACT GGT CTG CCA GCC TCA       1442
Pro Ser Ala Tyr Lys Asp Gln Val Ile Ala Thr Gly Leu Pro Ala Ser
            460                 465                 470

CCT GGG GCT GCT GTG GGC CAG GTT GTG TTC ACT GCT GAA GAT GCT GAA       1490
Pro Gly Ala Ala Val Gly Gln Val Val Phe Thr Ala Glu Asp Ala Glu
        475                 480                 485

GCA TGG CAT TCC CAA GGG AAA GCT GCT ATT CTG GTA AGG GCG GAG ACC       1538
Ala Trp His Ser Gln Gly Lys Ala Ala Ile Leu Val Arg Ala Glu Thr
```

-continued

| | | | | | | | | | | | | | | | | |
|---|---|---|---|---|---|---|---|---|---|---|---|---|---|---|---|---|
| 490 | | | | | 495 | | | | | 500 | | | | | 505 | |

```
AGC CCT GAG GAC GTT GGT GGC ATG CAC GCT GCT GTG GGG ATT CTT ACA       1586
Ser Pro Glu Asp Val Gly Gly Met His Ala Ala Val Gly Ile Leu Thr
            510                 515                 520

GAG AGG GGT GGC ATG ACT TCC CAC GCT GCT GTG GTC GCA CGT TGG TGG       1634
Glu Arg Gly Gly Met Thr Ser His Ala Ala Val Val Ala Arg Trp Trp
        525                 530                 535

GGG AAA TGC TGC GTC TCG GGA TGC TCA GGC ATT CGC GTA AAC GAT GCG       1682
Gly Lys Cys Cys Val Ser Gly Cys Ser Gly Ile Arg Val Asn Asp Ala
        540                 545                 550

GAG AAG CTC GTG ACG ATC GGA AGC CAT GTG CTG CGC GAA GGT GAG TGG       1730
Glu Lys Leu Val Thr Ile Gly Ser His Val Leu Arg Glu Gly Glu Trp
        555                 560                 565

CTG TCG CTG AAT GGG TCG ACT GGT GAG GTG ATC CTT GGG AAG CAG CCG       1778
Leu Ser Leu Asn Gly Ser Thr Gly Glu Val Ile Leu Gly Lys Gln Pro
570                 575                 580                 585

CTT TCC CCA CCA GCC CTT AGT GGT GAT CTG GGA ACT TTC ATG GCC TGG       1826
Leu Ser Pro Pro Ala Leu Ser Gly Asp Leu Gly Thr Phe Met Ala Trp
                590                 595                 600

GTG GAT GAT GTT AGA AAG CTC AAG GTC CTG GCT AAC GCC GAT ACC CCT       1874
Val Asp Asp Val Arg Lys Leu Lys Val Leu Ala Asn Ala Asp Thr Pro
            605                 610                 615

GAT GAT GCA TTG ACT GCG CGA AAC AAT GGG GCA CAA GGA ATT GGA TTA       1922
Asp Asp Ala Leu Thr Ala Arg Asn Asn Gly Ala Gln Gly Ile Gly Leu
        620                 625                 630

TGC CGG ACA GAG CAC ATG TTC TTT GCT TCA GAC GAG AGG ATT AAG GCT       1970
Cys Arg Thr Glu His Met Phe Phe Ala Ser Asp Glu Arg Ile Lys Ala
        635                 640                 645

GTC AGG CAG ATG ATT ATG GCT CCC ACG CTT GAG CTG AGG CAG CAG GCG       2018
Val Arg Gln Met Ile Met Ala Pro Thr Leu Glu Leu Arg Gln Gln Ala
650                 655                 660                 665

CTC GAC CGT CTC TTG ACG TAT CAG AGG TCT GAC TTC GAA GGC ATT TTC       2066
Leu Asp Arg Leu Leu Thr Tyr Gln Arg Ser Asp Phe Glu Gly Ile Phe
                670                 675                 680

CGT GCT ATG GAT GGA CTC CCG GTG ACC ATC CGA CTC CTG GAC CAT CCT       2114
Arg Ala Met Asp Gly Leu Pro Val Thr Ile Arg Leu Leu Asp His Pro
            685                 690                 695

TCT TAC GAG TTC CTT CCA GAA GGG AAC ATC GAG GAC ATT GTA AGT GAA       2162
Ser Tyr Glu Phe Leu Pro Glu Gly Asn Ile Glu Asp Ile Val Ser Glu
        700                 705                 710

TTA TGT GCT GAG ACG GGA GCC AAC CAG GAG GAT GCC CTC GCG CGA ATT       2210
Leu Cys Ala Glu Thr Gly Ala Asn Gln Glu Asp Ala Leu Ala Arg Ile
        715                 720                 725

GAA AAG CTT TCA GAA GTA AAC CCG ATG CTT GGC TTC CGT GGG TGC AGG       2258
Glu Lys Leu Ser Glu Val Asn Pro Met Leu Gly Phe Arg Gly Cys Arg
730                 735                 740                 745

CTT GGT ATA TCG TAC CCT GAA TTG ACA GAG ATG CAA GCC CGG GCC ATT       2306
Leu Gly Ile Ser Tyr Pro Glu Leu Thr Glu Met Gln Ala Arg Ala Ile
                750                 755                 760

TTT GAA GCT GCT ATA GCA ATG ACC AAC CAG GGT GTT CAA GTG TTC CCA       2354
Phe Glu Ala Ala Ile Ala Met Thr Asn Gln Gly Val Gln Val Phe Pro
            765                 770                 775

GAG ATA ATG GTT CCT CTT GTT GGA ACA CCA CAG GAA CTG GGG CAT CAA       2402
Glu Ile Met Val Pro Leu Val Gly Thr Pro Gln Glu Leu Gly His Gln
        780                 785                 790

GTG ACT CTT ATC CGC CAA GTT GCT GAG AAA GTG TTC GCC AAT GTG GGC       2450
Val Thr Leu Ile Arg Gln Val Ala Glu Lys Val Phe Ala Asn Val Gly
        795                 800                 805

AAG ACT ATC GGG TAC AAA GTT GGA ACA ATG ATT GAG ATC CCC AGG GCA       2498
Lys Thr Ile Gly Tyr Lys Val Gly Thr Met Ile Glu Ile Pro Arg Ala
```

```
                   810                   815                    820                    825
GCT CTG GTG GCT GAT GAG ATA GCG GAG CAG GCT GAA TTC TTC TCC TTC                   2546
Ala Leu Val Ala Asp Glu Ile Ala Glu Gln Ala Glu Phe Phe Ser Phe
                        830                    835                    840

GGA ACG AAC GAC CTG ACG CAG ATG ACC TTT GGG TAC AGC AGG GAT GAT                   2594
Gly Thr Asn Asp Leu Thr Gln Met Thr Phe Gly Tyr Ser Arg Asp Asp
                845                    850                    855

GTG GGA AAG TTC ATT CCC GTT CAT CTT GCT CAG GGC ATC CTC CAA CAT                   2642
Val Gly Lys Phe Ile Pro Val His Leu Ala Gln Gly Ile Leu Gln His
            860                    865                    870

GAC CCC TTC GAG GTC CTG GAC CAG AGG GGA GTG GGC GAG CTG GTG AAG                   2690
Asp Pro Phe Glu Val Leu Asp Gln Arg Gly Val Gly Glu Leu Val Lys
        875                    880                    885

TTT GCT ACA GAG AGG GGC CGC AAA GCT AGG CCT AAC TTG AAG GTG GGC                   2738
Phe Ala Thr Glu Arg Gly Arg Lys Ala Arg Pro Asn Leu Lys Val Gly
890                    895                    900                    905

ATT TGT GGA GAA CAC GGT GGA GAG CCT TCG TCT GTG GCC TTC TTC GCG                   2786
Ile Cys Gly Glu His Gly Gly Glu Pro Ser Ser Val Ala Phe Phe Ala
                    910                    915                    920

AAG GCT GGG CTG GAT TTC GTT TCT TGC TCC CCT TTC AGG GTT CCG ATT                   2834
Lys Ala Gly Leu Asp Phe Val Ser Cys Ser Pro Phe Arg Val Pro Ile
                925                    930                    935

GCT AGG CTA GCT GCA GCT CAG GTG CTT GTC TGAGGCTGCC TCCTCG                         2880
Ala Arg Leu Ala Ala Ala Gln Val Leu Val
            940                    945

(2) INFORMATION FOR SEQ ID NO:4:

(i) SEQUENCE CHARACTERISTICS:
        (A) LENGTH: 947 amino acids
        (B) TYPE: amino acid
        (D) TOPOLOGY: linear (ii) MOLECULE TYPE: protein (xi) SEQUENCE DESCRIPTION: SEQ ID NO:4:

Met Ala Ala Ser Val Ser Arg Ala Ile Cys Val Gln Lys Pro Gly Ser
     1               5                  10                  15

Lys Cys Thr Arg Asp Arg Glu Ala Thr Ser Phe Ala Arg Arg Ser Val
                    20                  25                  30

Ala Ala Pro Arg Pro His Ala Lys Ala Arg Arg His Pro Leu
                35                  40                  45

Arg Leu Arg Arg Gly Thr Gly Pro His Cys Ser Pro Leu Arg Ala Val
        50                  55                  60

Val Asp Ala Ala Pro Ile Gln Thr Thr Lys Lys Arg Val Phe His Phe
    65                  70                  75                  80

Gly Lys Gly Lys Ser Glu Gly Asn Lys Thr Met Lys Glu Leu Leu Gly
                    85                  90                  95

Gly Lys Gly Ala Asn Leu Ala Glu Met Ala Ser Ile Gly Leu Ser Val
                    100                 105                 110

Pro Pro Gly Phe Thr Val Ser Thr Glu Ala Cys Gln Gln Tyr Gln Asp
                115                 120                 125

Ala Gly Cys Ala Leu Pro Ala Gly Leu Trp Ala Glu Ile Val Asp Gly
            130                 135                 140

Leu Gln Trp Val Glu Glu Tyr Met Gly Ala Thr Leu Gly Asp Pro Gln
    145                 150                 155                 160

Arg Pro Leu Leu Leu Ser Val Arg Ser Gly Ala Ala Val Ser Met Pro
                    165                 170                 175

Gly Met Met Asp Thr Val Leu Asn Leu Gly Leu Asn Asp Glu Val Ala
```

```
                    180                 185                 190
Ala Gly Leu Ala Ala Lys Ser Gly Glu Arg Phe Ala Tyr Asp Ser Phe
                195                 200                 205
Arg Arg Phe Leu Asp Met Phe Gly Asn Val Val Met Asp Ile Pro Arg
210                 215                 220
Ser Leu Phe Glu Glu Lys Leu Glu His Met Lys Glu Ser Lys Gly Leu
225                 230                 235                 240
Lys Asn Asp Thr Asp Leu Thr Ala Ser Asp Leu Lys Glu Leu Val Gly
                245                 250                 255
Gln Tyr Lys Glu Val Tyr Leu Ser Ala Lys Gly Glu Pro Phe Pro Ser
                260                 265                 270
Asp Pro Lys Lys Gln Leu Glu Leu Ala Val Leu Ala Val Phe Asn Ser
                275                 280                 285
Trp Glu Ser Pro Arg Ala Lys Lys Tyr Arg Ser Ile Asn Gln Ile Thr
290                 295                 300
Gly Leu Arg Gly Thr Ala Val Asn Val Gln Cys Met Val Phe Gly Asn
305                 310                 315                 320
Met Gly Asn Thr Ser Gly Thr Gly Val Leu Phe Thr Arg Asn Pro Asn
                325                 330                 335
Thr Gly Glu Lys Lys Leu Tyr Gly Glu Phe Leu Val Asn Ala Gln Gly
                340                 345                 350
Glu Asp Val Val Ala Gly Ile Arg Thr Pro Glu Asp Leu Asp Ala Met
                355                 360                 365
Lys Asn Leu Met Pro Gln Ala Tyr Asp Glu Leu Val Glu Asn Cys Asn
                370                 375                 380
Ile Leu Glu Ser His Tyr Lys Glu Met Gln Asp Ile Glu Phe Thr Val
385                 390                 395                 400
Gln Glu Asn Arg Leu Trp Met Leu Gln Cys Arg Thr Gly Lys Arg Thr
                405                 410                 415
Gly Lys Ser Ala Val Lys Ile Ala Val Asp Met Val Asn Glu Gly Leu
                420                 425                 430
Val Glu Pro Arg Ser Ala Ile Lys Met Val Glu Pro Gly His Leu Asp
                435                 440                 445
Gln Leu Leu His Pro Gln Phe Glu Asn Pro Ser Ala Tyr Lys Asp Gln
                450                 455                 460
Val Ile Ala Thr Gly Leu Pro Ala Ser Pro Gly Ala Ala Val Gly Gln
465                 470                 475                 480
Val Val Phe Thr Ala Glu Asp Ala Glu Ala Trp His Ser Gln Gly Lys
                485                 490                 495
Ala Ala Ile Leu Val Arg Ala Gly Thr Ser Pro Glu Asp Val Gly Gly
                500                 505                 510
Met His Ala Ala Val Gly Ile Leu Thr Glu Arg Gly Gly Met Thr Ser
                515                 520                 525
His Ala Ala Val Val Ala Arg Trp Trp Gly Lys Cys Cys Val Ser Gly
                530                 535                 540
Cys Ser Gly Ile Arg Val Asn Asp Ala Glu Lys Leu Val Thr Ile Gly
545                 550                 555                 560
Ser His Val Leu Arg Glu Gly Glu Trp Leu Ser Leu Asn Gly Ser Thr
                565                 570                 575
Gly Glu Val Ile Leu Gly Lys Gln Pro Leu Ser Pro Pro Ala Leu Ser
                580                 585                 590
Gly Asp Leu Gly Thr Phe Met Ala Trp Val Asp Asp Val Arg Lys Leu
                595                 600                 605
```

```
Lys Val Leu Ala Asn Ala Asp Thr Pro Asp Asp Ala Leu Thr Ala Arg
    610                 615                 620
Asn Asn Gly Ala Gln Gly Ile Gly Leu Cys Arg Thr Glu His Met Phe
625                 630                 635                 640
Phe Ala Ser Asp Glu Arg Ile Lys Ala Val Arg Gln Met Ile Met Ala
                645                 650                 655
Pro Thr Leu Glu Leu Arg Gln Gln Ala Leu Asp Arg Leu Leu Thr Tyr
                660                 665                 670
Gln Arg Ser Asp Phe Glu Gly Ile Phe Arg Ala Met Asp Gly Leu Pro
            675                 680                 685
Val Thr Ile Arg Leu Leu Asp His Pro Ser Tyr Glu Phe Leu Pro Glu
        690                 695                 700
Gly Asn Ile Glu Asp Ile Val Ser Glu Leu Cys Ala Glu Thr Gly Ala
705                 710                 715                 720
Asn Gln Glu Asp Ala Leu Ala Arg Ile Glu Lys Leu Ser Glu Val Asn
                725                 730                 735
Pro Met Leu Gly Phe Arg Gly Cys Arg Leu Gly Ile Ser Tyr Pro Glu
            740                 745                 750
Leu Thr Glu Met Gln Ala Arg Ala Ile Phe Glu Ala Ala Ile Ala Met
        755                 760                 765
Thr Asn Gln Gly Val Gln Val Phe Pro Glu Ile Met Val Pro Leu Val
770                 775                 780
Gly Thr Pro Gln Glu Leu Gly His Gln Val Thr Leu Ile Arg Gln Val
785                 790                 795                 800
Ala Glu Lys Val Phe Ala Asn Val Gly Lys Thr Ile Gly Tyr Lys Val
                805                 810                 815
Gly Thr Met Ile Glu Ile Pro Arg Ala Ala Leu Val Ala Asp Glu Ile
            820                 825                 830
Ala Glu Gln Ala Glu Phe Phe Ser Phe Gly Thr Asn Asp Leu Thr Gln
        835                 840                 845
Met Thr Phe Gly Tyr Ser Arg Asp Asp Val Gly Lys Phe Ile Pro Val
850                 855                 860
His Leu Ala Gln Gly Ile Leu Gln His Asp Pro Phe Glu Val Leu Asp
865                 870                 875                 880
Gln Arg Gly Val Gly Glu Leu Val Lys Phe Ala Thr Glu Arg Gly Arg
                885                 890                 895
Lys Ala Arg Pro Asn Leu Lys Val Gly Ile Cys Gly Glu His Gly Gly
            900                 905                 910
Glu Pro Ser Ser Val Ala Phe Phe Ala Lys Ala Gly Leu Asp Phe Val
        915                 920                 925
Ser Cys Ser Pro Phe Arg Val Pro Ile Ala Arg Leu Ala Ala Ala Gln
930                 935                 940
Val Leu Val
945

(2) INFORMATION FOR SEQ ID NO:5:

(i) SEQUENCE CHARACTERISTICS:
        (A) LENGTH: 2610 base pairs
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: CDS
        (B) LOCATION: 70..2589
```

(xi) SEQUENCE DESCRIPTION: SEQ ID NO:5:

```
GAATTCTCAA TCCTTTGCTC ATCGCAGCAT ATCAATGTTA ACACATAAAC TTTAGGAGGA         60

AGAAAACTT ATG GCA AAA TGG GTT TAT AAG TTC GAA GAA GGC AAT GCA            108
          Met Ala Lys Trp Val Tyr Lys Phe Glu Glu Gly Asn Ala
            1               5                  10

TCT ATG AGA AAC CTT CTT GGA GGC AAA GGC TGC AAC CTT GCA GAG ATG          156
Ser Met Arg Asn Leu Leu Gly Gly Lys Gly Cys Asn Leu Ala Glu Met
 15                  20                  25

ACC ATC TTA GGA ATG CCG ATT CCA CAG GGC TTT ACT GTA ACA ACA GAA          204
Thr Ile Leu Gly Met Pro Ile Pro Gln Gly Phe Thr Val Thr Thr Glu
 30                  35                  40                  45

GCT TGT ACA GAG TAC TAC AAC AGT GGA AAA CAG ATC ACA CAG GAA ATT          252
Ala Cys Thr Glu Tyr Tyr Asn Ser Gly Lys Gln Ile Thr Gln Glu Ile
                 50                  55                  60

CAG GAT CAG ATT TTC GAA GCT ATC ACA TGG TTA GAG GAA CTG AAC GGC          300
Gln Asp Gln Ile Phe Glu Ala Ile Thr Trp Leu Glu Glu Leu Asn Gly
             65                  70                  75

AAG AAG TTC GGC GAC ACT GAA GAT CCG TTA TTA GTA TCT GTA CGT TCC          348
Lys Lys Phe Gly Asp Thr Glu Asp Pro Leu Leu Val Ser Val Arg Ser
         80                  85                  90

GCG GCC CGC GCA TCC ATG CCG GGT ATG ATG GAT ACC ATC CTG AAC CTT          396
Ala Ala Arg Ala Ser Met Pro Gly Met Met Asp Thr Ile Leu Asn Leu
 95                 100                 105

GGT TTA AAC GAC GTT GCA GTA GAG GGC TTT GCA AAG AAA ACG GGA AAT          444
Gly Leu Asn Asp Val Ala Val Glu Gly Phe Ala Lys Lys Thr Gly Asn
110                 115                 120                 125

CCA AGA TTT GCA TAT GAT TCT TAC AGA AGA TTT ATC CAG ATG TAT TCC          492
Pro Arg Phe Ala Tyr Asp Ser Tyr Arg Arg Phe Ile Gln Met Tyr Ser
                130                 135                 140

GAC GTA GTT ATG GAA GTT CCG AAG TCC CAT TTC GAG AAA ATC ATC GAT          540
Asp Val Val Met Glu Val Pro Lys Ser His Phe Glu Lys Ile Ile Asp
            145                 150                 155

GCG ATG AAA GAA GAA AAG GGC GTT CAC TTC GAT ACA GAC CTG ACT GCC          588
Ala Met Lys Glu Glu Lys Gly Val His Phe Asp Thr Asp Leu Thr Ala
        160                 165                 170

GAT GAT TTA AAA GAG CTG GCT GAG AAG TTC AAA GCT GTT TAC AAA GAG          636
Asp Asp Leu Lys Glu Leu Ala Glu Lys Phe Lys Ala Val Tyr Lys Glu
175                 180                 185

GCT ATG AAC GGC GAA GAG TTC CCA CAG GAG CCG AAG GAT CAG TTA ATG          684
Ala Met Asn Gly Glu Glu Phe Pro Gln Glu Pro Lys Asp Gln Leu Met
190                 195                 200                 205

GGC GCT GTT AAA GCA GTT TTC CGT TCC TGG GAC AAC CCT CGT GCA ATC          732
Gly Ala Val Lys Ala Val Phe Arg Ser Trp Asp Asn Pro Arg Ala Ile
                210                 215                 220

GTA TAC CGC CGT ATG AAC GAT ATC CCT GGA GAC TGG GGT ACT GCA GTT          780
Val Tyr Arg Arg Met Asn Asp Ile Pro Gly Asp Trp Gly Thr Ala Val
            225                 230                 235

AAC GTT CAG ACC ATG GTA TTT GGT AAC AAG GGC GAG ACC AGC GGT ACA          828
Asn Val Gln Thr Met Val Phe Gly Asn Lys Gly Glu Thr Ser Gly Thr
        240                 245                 250

GGC GTT GCC TTC ACA CGT AAC CCA TCC ACA GGT GAA AAA GGC ATC TAC          876
Gly Val Ala Phe Thr Arg Asn Pro Ser Thr Gly Glu Lys Gly Ile Tyr
255                 260                 265

GGT GAG TAC CTG ATC AAT GCA CAG GGC GAG GAC GTA GTT GCA GGT GTC          924
Gly Glu Tyr Leu Ile Asn Ala Gln Gly Glu Asp Val Val Ala Gly Val
270                 275                 280                 285

CGC ACA CCA CAG CCT ATC ACC CAG TTA GAG AAC GAT ATG CCT GAC TGC          972
Arg Thr Pro Gln Pro Ile Thr Gln Leu Glu Asn Asp Met Pro Asp Cys
                290                 295                 300
```

```
TAC AAG CAG TTC ATG GAT CTG GCC ATG AAG CTG GAG AAA CAT TTC CGT       1020
Tyr Lys Gln Phe Met Asp Leu Ala Met Lys Leu Glu Lys His Phe Arg
            305                 310                 315

GAC ATG CAG GAT ATG GAG TTC ACA ATC GAG GAA GGT AAA TTA TAC TTC       1068
Asp Met Gln Asp Met Glu Phe Thr Ile Glu Glu Gly Lys Leu Tyr Phe
            320                 325                 330

TTA CAG ACA CGT AAC GGC AAG AGA ACA GCT CCG GCT GCT CTT CAG ATT       1116
Leu Gln Thr Arg Asn Gly Lys Arg Thr Ala Pro Ala Ala Leu Gln Ile
        335                 340                 345

GCC TGC GAT TTA GTA GAC GAA GGC ATG ATC ACA GAG GAA GAG GCT GTT       1164
Ala Cys Asp Leu Val Asp Glu Gly Met Ile Thr Glu Glu Glu Ala Val
350                 355                 360                 365

GTA AGA ATC GAA GCA AAA TCT CTT GAT CAG TTA CTT CAC CCG ACC TTC       1212
Val Arg Ile Glu Ala Lys Ser Leu Asp Gln Leu Leu His Pro Thr Phe
                370                 375                 380

AAC CCG GCT GCT TTA AAG GCC GGC GAA GTA ATC GGT TCC GCT CTT CCG       1260
Asn Pro Ala Ala Leu Lys Ala Gly Glu Val Ile Gly Ser Ala Leu Pro
            385                 390                 395

GCA TCT CCT GGC GCA GCA GCA GGT AAA GTA TAC TTC ACC GCT GAT GAG       1308
Ala Ser Pro Gly Ala Ala Ala Gly Lys Val Tyr Phe Thr Ala Asp Glu
            400                 405                 410

GCT AAG GCT GCC CAC GAG AAG GGT GAG AGA GTT ATC CTT GTT CGT CTT       1356
Ala Lys Ala Ala His Glu Lys Gly Glu Arg Val Ile Leu Val Arg Leu
        415                 420                 425

GAG ACA TCT CCG GAA GAT ATC GAA GGT ATG CAT GCA GCC GAA GGT ATC       1404
Glu Thr Ser Pro Glu Asp Ile Glu Gly Met His Ala Ala Glu Gly Ile
430                 435                 440                 445

CTG ACA GTG CGC GGC GGT ATG ACA AGC CAT GCA GCC GTA GTT GCA CGT       1452
Leu Thr Val Arg Gly Gly Met Thr Ser His Ala Ala Val Val Ala Arg
                450                 455                 460

GGT ATG GGA ACA TGC TGC GTA TCC GGA TGC GGT GAG ATC AAG ATC AAC       1500
Gly Met Gly Thr Cys Cys Val Ser Gly Cys Gly Glu Ile Lys Ile Asn
            465                 470                 475

GAA GAA GCT AAG ACA TTC GAA CTT GGC GGA CAC ACA TTT GCA GAG GGA       1548
Glu Glu Ala Lys Thr Phe Glu Leu Gly Gly His Thr Phe Ala Glu Gly
            480                 485                 490

GAT TAC ATC TCC TTA GAT GGT TCC ACA GGT AAG ATT TAC AAG GGC GAC       1596
Asp Tyr Ile Ser Leu Asp Gly Ser Thr Gly Lys Ile Tyr Lys Gly Asp
        495                 500                 505

ATC GAG ACT CAG GAA CGT TCC GTA AGC GGA AGC TTC GAG CGT ATC ATG       1644
Ile Glu Thr Gln Glu Arg Ser Val Ser Gly Ser Phe Glu Arg Ile Met
510                 515                 520                 525

GTA TGG GCT GAC AAG TTC AGA ACA TTA AAG GTT CGT ACA AAT GCC GAC       1692
Val Trp Ala Asp Lys Phe Arg Thr Leu Lys Val Arg Thr Asn Ala Asp
                530                 535                 540

ACA CCG GAA GAT ACA CTC AAT GCC GTT AAA CTG GGT GCA GAG GGC ATC       1740
Thr Pro Glu Asp Thr Leu Asn Ala Val Lys Leu Gly Ala Glu Gly Ile
            545                 550                 555

GGT CTT TGC CGT ACA GAG CAT ATG TTC TTC GAG GCT GAC AGA ATC ATG       1788
Gly Leu Cys Arg Thr Glu His Met Phe Phe Glu Ala Asp Arg Ile Met
            560                 565                 570

AAG ATC AGA AAG ATG ATC CTT TCC GAT TCA GTG GAA GCA AGA GAA GAG       1836
Lys Ile Arg Lys Met Ile Leu Ser Asp Ser Val Glu Ala Arg Glu Glu
        575                 580                 585

GCT CTG AAC GAA TTA ATC CCG TTC CAG AAG GGC GAT TTC AAG GCT ATG       1884
Ala Leu Asn Glu Leu Ile Pro Phe Gln Lys Gly Asp Phe Lys Ala Met
590                 595                 600                 605

TAC AAA GCT CTG GAA GGC AGG CCA ATG ACG GTT CGC TAC CTG GAT CCG       1932
Tyr Lys Ala Leu Glu Gly Arg Pro Met Thr Val Arg Tyr Leu Asp Pro
                610                 615                 620
```

```
CCG CTG CAT GAG TTC GTT CCT CAT ACA GAA GAG GAG CAG GCT GAA CTG     1980
Pro Leu His Glu Phe Val Pro His Thr Glu Glu Glu Gln Ala Glu Leu
        625                 630                 635

GCT AAG AAC ATG GGC CTT ACT TTA GCA GAA GTA AAA GCA AAA GTT GAC     2028
Ala Lys Asn Met Gly Leu Thr Leu Ala Glu Val Lys Ala Lys Val Asp
            640                 645                 650

GAA TTA CAC GAG TTC AAC CCA ATG ATG GGC CAT CGT GGC TGC CGT CTT     2076
Glu Leu His Glu Phe Asn Pro Met Met Gly His Arg Gly Cys Arg Leu
        655                 660                 665

GCA GTT ACC TAT CCG GAA ATT GCA AAG ATG CAG ACA AGA GCC GTT ATG     2124
Ala Val Thr Tyr Pro Glu Ile Ala Lys Met Gln Thr Arg Ala Val Met
670                 675                 680                 685

GAA GCT GCT ATC GAA GTG AAG GAA GAG ACA GGA ATC GAT ATT GTT CCT     2172
Glu Ala Ala Ile Glu Val Lys Glu Glu Thr Gly Ile Asp Ile Val Pro
                690                 695                 700

GAG ATC ATG ATT CCG TTA GTT GGC GAG AAG AAA GAG CTT AAG TTC GTT     2220
Glu Ile Met Ile Pro Leu Val Gly Glu Lys Lys Glu Leu Lys Phe Val
            705                 710                 715

AAG GAC GTA GTT GTG GAA GTA GCT GAG CAG GTT AAG AAA GAG AAA GGT     2268
Lys Asp Val Val Val Glu Val Ala Glu Gln Val Lys Lys Glu Lys Gly
        720                 725                 730

TCC GAT ATG CAG TAC CAC ATC GGT ACC ATG ATC GAA ATT CCT CGT GCA     2316
Ser Asp Met Gln Tyr His Ile Gly Thr Met Ile Glu Ile Pro Arg Ala
735                 740                 745

GCT CTC ACA GCA GAT GCC ATC GCT GAG GAA GCA GAG TTC TTC TCC TTC     2364
Ala Leu Thr Ala Asp Ala Ile Ala Glu Glu Ala Glu Phe Phe Ser Phe
750                 755                 760                 765

GGT ACA AAC GAC TTA ACA CAG ATG ACA TTC GGC TTC TCC CGT GAC GAC     2412
Gly Thr Asn Asp Leu Thr Gln Met Thr Phe Gly Phe Ser Arg Asp Asp
                770                 775                 780

GCC GGC AAG TTC CTG GAT TCC TAC TAT AAA GCA AAA ATT TAT GAG TCC     2460
Ala Gly Lys Phe Leu Asp Ser Tyr Tyr Lys Ala Lys Ile Tyr Glu Ser
            785                 790                 795

GAT CCA TTC GCA AGA CTT GAC CAG ACA GGC GTT GGC CAG TTA GTA GAG     2508
Asp Pro Phe Ala Arg Leu Asp Gln Thr Gly Val Gly Gln Leu Val Glu
        800                 805                 810

ATG GCA GTT AAG AAA GGC CGT CAG ACA CGT CCG GGC CTT AAG TGC GGC     2556
Met Ala Val Lys Lys Gly Arg Gln Thr Arg Pro Gly Leu Lys Cys Gly
815                 820                 825

ATC TGC GGC GAG CAC GGC GAG ATC CTT CTT CCG TAGAGTTCTG CCACAAAGTA   2609
Ile Cys Gly Glu His Gly Glu Ile Leu Leu Pro
830                 835                 840

G                                                                   2610
```

(2) INFORMATION FOR SEQ ID NO:6:

(i) SEQUENCE CHARACTERISTICS:
        (A) LENGTH: 840 amino acids
        (B) TYPE: amino acid
        (D) TOPOLOGY: linear (ii) MOLECULE TYPE: protein (xi) SEQUENCE DESCRIPTION: SEQ ID NO:6:

```
Met Ala Lys Trp Val Tyr Lys Phe Glu Glu Gly Asn Ala Ser Met Arg
1               5                   10                  15

Asn Leu Leu Gly Gly Lys Gly Cys Asn Leu Ala Glu Met Thr Ile Leu
            20                  25                  30

Gly Met Pro Ile Pro Gln Gly Phe Thr Val Thr Glu Ala Cys Thr
        35                  40                  45
```

```
Glu Tyr Tyr Asn Ser Gly Lys Gln Ile Thr Gln Glu Ile Gln Asp Gln
 50                  55                  60

Ile Phe Glu Ala Ile Thr Trp Leu Glu Glu Leu Asn Gly Lys Lys Phe
 65                  70                  75                  80

Gly Asp Thr Glu Asp Pro Leu Leu Val Ser Val Arg Ser Ala Ala Arg
                 85                  90                  95

Ala Ser Met Pro Gly Met Met Asp Thr Ile Leu Asn Leu Gly Leu Asn
                100                 105                 110

Asp Val Ala Val Glu Gly Phe Ala Lys Lys Thr Gly Asn Pro Arg Phe
            115                 120                 125

Ala Tyr Asp Ser Tyr Arg Arg Phe Ile Gln Met Tyr Ser Asp Val Val
    130                 135                 140

Met Glu Val Pro Lys Ser His Phe Glu Lys Ile Ile Asp Ala Met Lys
145                 150                 155                 160

Glu Glu Lys Gly Val His Phe Asp Thr Asp Leu Thr Ala Asp Asp Leu
                165                 170                 175

Lys Glu Leu Ala Glu Lys Phe Lys Ala Val Tyr Lys Glu Ala Met Asn
            180                 185                 190

Gly Glu Glu Phe Pro Gln Glu Pro Lys Asp Gln Leu Met Gly Ala Val
        195                 200                 205

Lys Ala Val Phe Arg Ser Trp Asp Asn Pro Arg Ala Ile Val Tyr Arg
210                 215                 220

Arg Met Asn Asp Ile Pro Gly Asp Trp Gly Thr Ala Val Asn Val Gln
225                 230                 235                 240

Thr Met Val Phe Gly Asn Lys Gly Glu Thr Ser Gly Thr Gly Val Ala
                245                 250                 255

Phe Thr Arg Asn Pro Ser Thr Gly Glu Lys Gly Ile Tyr Gly Glu Tyr
            260                 265                 270

Leu Ile Asn Ala Gln Gly Glu Asp Val Val Ala Gly Val Arg Thr Pro
        275                 280                 285

Gln Pro Ile Thr Gln Leu Glu Asn Asp Met Pro Asp Cys Tyr Lys Gln
290                 295                 300

Phe Met Asp Leu Ala Met Lys Leu Glu Lys His Phe Arg Asp Met Gln
305                 310                 315                 320

Asp Met Glu Phe Thr Ile Glu Glu Gly Lys Leu Tyr Phe Leu Gln Thr
                325                 330                 335

Arg Asn Gly Lys Arg Thr Ala Pro Ala Ala Leu Gln Ile Ala Cys Asp
            340                 345                 350

Leu Val Asp Glu Gly Met Ile Thr Glu Glu Ala Val Val Arg Ile
        355                 360                 365

Glu Ala Lys Ser Leu Asp Gln Leu Leu His Pro Thr Phe Asn Pro Ala
370                 375                 380

Ala Leu Lys Ala Gly Glu Val Ile Gly Ser Ala Leu Pro Ala Ser Pro
385                 390                 395                 400

Gly Ala Ala Ala Gly Lys Val Tyr Phe Thr Ala Asp Glu Ala Lys Ala
                405                 410                 415

Ala His Glu Lys Gly Glu Arg Val Ile Leu Val Arg Leu Glu Thr Ser
            420                 425                 430

Pro Glu Asp Ile Glu Gly Met His Ala Ala Gly Ile Leu Thr Val
        435                 440                 445

Arg Gly Gly Met Thr Ser His Ala Ala Val Val Ala Arg Gly Met Gly
    450                 455                 460

Thr Cys Cys Val Ser Gly Cys Gly Glu Ile Lys Ile Asn Glu Glu Ala
465                 470                 475                 480
```

-continued

```
Lys Thr Phe Glu Leu Gly Gly His Thr Phe Ala Glu Gly Asp Tyr Ile
                485                 490                 495
Ser Leu Asp Gly Ser Thr Gly Lys Ile Tyr Lys Gly Asp Ile Glu Thr
            500                 505                 510
Gln Glu Arg Ser Val Ser Gly Ser Phe Glu Arg Ile Met Val Trp Ala
        515                 520                 525
Asp Lys Phe Arg Thr Leu Lys Val Arg Thr Asn Ala Asp Thr Pro Glu
    530                 535                 540
Asp Thr Leu Asn Ala Val Lys Leu Gly Ala Glu Gly Ile Gly Leu Cys
545                 550                 555                 560
Arg Thr Glu His Met Phe Phe Glu Ala Asp Arg Ile Met Lys Ile Arg
                565                 570                 575
Lys Met Ile Leu Ser Asp Ser Val Glu Ala Arg Glu Glu Ala Leu Asn
            580                 585                 590
Glu Leu Ile Pro Phe Gln Lys Gly Asp Phe Lys Ala Met Tyr Lys Ala
        595                 600                 605
Leu Glu Gly Arg Pro Met Thr Val Arg Tyr Leu Asp Pro Pro Leu His
    610                 615                 620
Glu Phe Val Pro His Thr Glu Glu Gln Ala Glu Leu Ala Lys Asn
625                 630                 635                 640
Met Gly Leu Thr Leu Ala Glu Val Lys Ala Lys Val Asp Glu Leu His
                645                 650                 655
Glu Phe Asn Pro Met Met Gly His Arg Gly Cys Arg Leu Ala Val Thr
            660                 665                 670
Tyr Pro Glu Ile Ala Lys Met Gln Thr Arg Ala Val Met Glu Ala Ala
        675                 680                 685
Ile Glu Val Lys Glu Glu Thr Gly Ile Asp Ile Val Pro Glu Ile Met
    690                 695                 700
Ile Pro Leu Val Gly Glu Lys Lys Glu Leu Lys Phe Val Lys Asp Val
705                 710                 715                 720
Val Val Glu Val Ala Glu Gln Val Lys Lys Glu Lys Gly Ser Asp Met
                725                 730                 735
Gln Tyr His Ile Gly Thr Met Ile Glu Ile Pro Arg Ala Ala Leu Thr
            740                 745                 750
Ala Asp Ala Ile Ala Glu Glu Ala Glu Phe Phe Ser Phe Gly Thr Asn
        755                 760                 765
Asp Leu Thr Gln Met Thr Phe Gly Phe Ser Arg Asp Asp Ala Gly Lys
    770                 775                 780
Phe Leu Asp Ser Tyr Tyr Lys Ala Lys Ile Tyr Glu Ser Asp Pro Phe
785                 790                 795                 800
Ala Arg Leu Asp Gln Thr Gly Val Gly Gln Leu Val Glu Met Ala Val
                805                 810                 815
Lys Lys Gly Arg Gln Thr Arg Pro Gly Leu Lys Cys Gly Ile Cys Gly
            820                 825                 830
Glu His Gly Glu Ile Leu Leu Pro
        835                 840
```

(2) INFORMATION FOR SEQ ID NO:7:

(i) SEQUENCE CHARACTERISTICS:
        (A) LENGTH: 2722 base pairs
        (B) TYPE: nucleic acid
        (C) STRANDEDNESS: single
        (D) TOPOLOGY: linear (ii) MOLECULE TYPE: other nucleic acid (ix) FEATURE:
  (A) NAME/KEY: CDS
  (B) LOCATION: 48..2702

(xi) SEQUENCE DESCRIPTION: SEQ ID NO:7:

```
GAACTATTTA AGGAATTTGT AAGAATTTAG AGTTCATTCA GATAATA ATG CAA AGA         56
                                                    Met Gln Arg
                                                      1

GTA TAT GCT TTC GAA GAT GGT GAT GGA ACC AAC AAG AAA CTC CTT GGA        104
Val Tyr Ala Phe Glu Asp Gly Asp Gly Thr Asn Lys Lys Leu Leu Gly
      5                  10                  15

GGA AAG GGA GCT GGA CTT TGC ACA ATG ACA AAA ATT GGA CTT CCA GTT        152
Gly Lys Gly Ala Gly Leu Cys Thr Met Thr Lys Ile Gly Leu Pro Val
 20                  25                  30                  35

CCA CAA GGA TTT GTT ATT ACA ACT GAA ATG TGT AAA CAA TTC ATT GCT        200
Pro Gln Gly Phe Val Ile Thr Thr Glu Met Cys Lys Gln Phe Ile Ala
                  40                  45                  50

AAT GGA AAC AAA ATG CCA GAA GGA TTA ATG GAA GAA GTT AAA AAA GAA        248
Asn Gly Asn Lys Met Pro Glu Gly Leu Met Glu Glu Val Lys Lys Glu
             55                  60                  65

TAT CAA TTA GTT GAA AAG AAA TCA GGA AAA GTC TTT GGA GGA GAA GAA        296
Tyr Gln Leu Val Glu Lys Lys Ser Gly Lys Val Phe Gly Gly Glu Glu
         70                  75                  80

AAT CCA CTT CTT GTT TCA GTC AGA TCA GGA GCT GCT ATG TCT ATG CCA        344
Asn Pro Leu Leu Val Ser Val Arg Ser Gly Ala Ala Met Ser Met Pro
     85                  90                  95

GGT ATG ATG GAT ACT ATT CTT AAT CTT GGA CTT AAT GAT AAA ACT GTT        392
Gly Met Met Asp Thr Ile Leu Asn Leu Gly Leu Asn Asp Lys Thr Val
100                 105                 110                 115

GTT GCT CTT GCT AAA TTA ACC AAC AAT GAA AGA TTT GCA TAT GAT TCA        440
Val Ala Leu Ala Lys Leu Thr Asn Asn Glu Arg Phe Ala Tyr Asp Ser
                120                 125                 130

TAC AGA AGA TTT GTT TCC CTC TTC GGA AAG ATT GCT CTT AAT GCT TGT        488
Tyr Arg Arg Phe Val Ser Leu Phe Gly Lys Ile Ala Leu Asn Ala Cys
            135                 140                 145

GAT GAA GTT TAT GAT AAG ACT CTT GAA AAC AAA AAA GTT GAA AAG GGA        536
Asp Glu Val Tyr Asp Lys Thr Leu Glu Asn Lys Lys Val Glu Lys Gly
        150                 155                 160

GTT AAA TTA GAT ACT GAA TTA GAT GCT AAT GAT ATG AAA GAA CTT GCA        584
Val Lys Leu Asp Thr Glu Leu Asp Ala Asn Asp Met Lys Glu Leu Ala
    165                 170                 175

CAA GTC TTC ATT AAA AAG ACT GAA GAA TTC ACT AAA CAA CCA TTC CCA        632
Gln Val Phe Ile Lys Lys Thr Glu Glu Phe Thr Lys Gln Pro Phe Pro
180                 185                 190                 195

GTT GAT CCA TAT GCT CAA TTA GAA TTT GCC ATT TGT GCT GTA TTC AGA        680
Val Asp Pro Tyr Ala Gln Leu Glu Phe Ala Ile Cys Ala Val Phe Arg
                200                 205                 210

TCA TGG ATG GGA AAG AGA GCT GTT GAT TAC AGA AGA GAA TTC AAG ATT        728
Ser Trp Met Gly Lys Arg Ala Val Asp Tyr Arg Arg Glu Phe Lys Ile
            215                 220                 225

ACT CCA GAA CAA GCT GAT GGA ACT GCT GTT TCA GTT GTT TCT ATG GTT        776
Thr Pro Glu Gln Ala Asp Gly Thr Ala Val Ser Val Val Ser Met Val
        230                 235                 240

TAT GGT AAT ATG GGT AAT GAT TCA GCT ACT GGT GTT TGT TTC ACT AGA        824
Tyr Gly Asn Met Gly Asn Asp Ser Ala Thr Gly Val Cys Phe Thr Arg
    245                 250                 255

GAT CCA GGA ACA GGA GAA AAT ATG TTC TTC GGA GAA TAT CTT AAG AAT        872
Asp Pro Gly Thr Gly Glu Asn Met Phe Phe Gly Glu Tyr Leu Lys Asn
260                 265                 270                 275

GCA CAA GGA GAA GAT GTT GTT GCT GGT ATT AGA ACA CCA CAA ATT ATT        920
Ala Gln Gly Glu Asp Val Val Ala Gly Ile Arg Thr Pro Gln Ile Ile
```

```
            Ala Gln Gly Glu Asp Val Val Ala Gly Ile Arg Thr Pro Gln Ile Ile
                            280                 285                 290

TCA AAG ATG GCA GAA GAT CGA GAT CTT CCA GGT TGC TAT GAA CAA CTT                 968
Ser Lys Met Ala Glu Asp Arg Asp Leu Pro Gly Cys Tyr Glu Gln Leu
            295                 300                 305

CTT GAT ATT AGA AAG AAA TTA GAA GGA TAT TTC CAT GAA GTA CAA GAC                1016
Leu Asp Ile Arg Lys Lys Leu Glu Gly Tyr Phe His Glu Val Gln Asp
            310                 315                 320

TTT GAA TTC ACT ATT GAA AGA AAG AAA CTT TAC ATG CTC CAA ACT AGA                1064
Phe Glu Phe Thr Ile Glu Arg Lys Lys Leu Tyr Met Leu Gln Thr Arg
        325                 330                 335

AAT GGA AAG ATG AAT GCA ACT GCT ACT GTC AGA ACA GGA GTT GAT ATG                1112
Asn Gly Lys Met Asn Ala Thr Ala Thr Val Arg Thr Gly Val Asp Met
340                 345                 350                 355

GTT GAA GAA GGA CTT ATT ACA AAA GAA CAA GCC ATT ATG AGA ATT GCA                1160
Val Glu Glu Gly Leu Ile Thr Lys Glu Gln Ala Ile Met Arg Ile Ala
                360                 365                 370

CCA CAA TCA GTT GAT CAA TTA CTT CAT AAG AAT ATG CCA GCT AAT TAT                1208
Pro Gln Ser Val Asp Gln Leu Leu His Lys Asn Met Pro Ala Asn Tyr
            375                 380                 385

GCA GAA GCT CCA TTA GTT AAA GGA CTT CCA GCA TCA CCA GGA GCT GCT                1256
Ala Glu Ala Pro Leu Val Lys Gly Leu Pro Ala Ser Pro Gly Ala Ala
            390                 395                 400

ACA GGA GCT GTT GTT TTT GAT GCC GAT GAT GCA GTT GAA CAA GCT AAA                1304
Thr Gly Ala Val Val Phe Asp Ala Asp Asp Ala Val Glu Gln Ala Lys
        405                 410                 415

GGA AAG AAA GTT CTT CTT CTT AGA GAA GAA ACT AAA CCA GAA GAT ATT                1352
Gly Lys Lys Val Leu Leu Leu Arg Glu Glu Thr Lys Pro Glu Asp Ile
420                 425                 430                 435

CAT GGA TTC TTT GTT GCT GAA GGT ATT TTA ACC TGC AGA GGA GGA AAA                1400
His Gly Phe Phe Val Ala Glu Gly Ile Leu Thr Cys Arg Gly Gly Lys
                440                 445                 450

ACA TCA CAC GCA GCT GTC GTT GCT AGA GGT ATG GGT AAA CCA TGT GTT                1448
Thr Ser His Ala Ala Val Val Ala Arg Gly Met Gly Lys Pro Cys Val
            455                 460                 465

TCA GGA GCT GAA GGA ATT AAA GTT GAT GTT GCT AAG AAA ATT GCT AAG                1496
Ser Gly Ala Glu Gly Ile Lys Val Asp Val Ala Lys Lys Ile Ala Lys
            470                 475                 480

ATT GGA AGC CTT GAA GTT CAT GAA GGA GAT ATT TTA ACT ATT GAT GGA                1544
Ile Gly Ser Leu Glu Val His Glu Gly Asp Ile Leu Thr Ile Asp Gly
        485                 490                 495

TCA ACT GGA TGT GTC TAT AAG GGA GAA GTT CCA TTA GAA GAA CCA CAA                1592
Ser Thr Gly Cys Val Tyr Lys Gly Glu Val Pro Leu Glu Glu Pro Gln
500                 505                 510                 515

GTT GGA TCA GGA TAT TTC GGA ACC ATC TTA AAA TGG GCC AAT GAA ATT                1640
Val Gly Ser Gly Tyr Phe Gly Thr Ile Leu Lys Trp Ala Asn Glu Ile
                520                 525                 530

AAA AAG ATT GGA GTT TTT GCT GCT GGA GAT CTT CCA TCA GCT GCT AAG                1688
Lys Lys Ile Gly Val Phe Ala Ala Gly Asp Leu Pro Ser Ala Ala Lys
            535                 540                 545

AAA GCC CTT GAA TTT GGA GCT GAA GGT ATT GGA CTT TGC AGA ACT GAA                1736
Lys Ala Leu Glu Phe Gly Ala Glu Gly Ile Gly Leu Cys Arg Thr Glu
            550                 555                 560

CGT ATG TTC AAT GCA GTT GAA AGA CTT CCA ATT GTT GTC AAG ATG ATT                1784
Arg Met Phe Asn Ala Val Glu Arg Leu Pro Ile Val Val Lys Met Ile
        565                 570                 575

CTT TCA AAT ACC CTT GAA GAA AGA AAG AAA TAT CTT AAT GAA CTT ATG                1832
Leu Ser Asn Thr Leu Glu Glu Arg Lys Lys Tyr Leu Asn Glu Leu Met
580                 585                 590                 595

CCA CTT CAA AAA CAA GAT TTC ATT GGA TTA TTG AAG ACT ATG AAT GGA                1880
Pro Leu Gln Lys Gln Asp Phe Ile Gly Leu Leu Lys Thr Met Asn Gly
```

-continued

```
Pro Leu Gln Lys Gln Asp Phe Ile Gly Leu Leu Lys Thr Met Asn Gly
            600                 605                 610

CTT CCA GTC ACT GTC AGA CTT CTT GAT CCA CCA TTA CAT GAA TTC CTC      1928
Leu Pro Val Thr Val Arg Leu Leu Asp Pro Pro Leu His Glu Phe Leu
                615                 620                 625

CCA ACT CTT GAA GAG TTA ATG AGA GAA ATC TTT GAA ATG AAA CTT TCA      1976
Pro Thr Leu Glu Glu Leu Met Arg Glu Ile Phe Glu Met Lys Leu Ser
            630                 635                 640

GGT AAG ACT GAA GGA CTT GCA GAA AAA GAA GTT GTT CTT AAG AAA GTT      2024
Gly Lys Thr Glu Gly Leu Ala Glu Lys Glu Val Val Leu Lys Lys Val
        645                 650                 655

AAA GAA CTT ATG GAA GTT AAT CCA ATG ATT GGA CAC AGA GGA ATT AGA      2072
Lys Glu Leu Met Glu Val Asn Pro Met Ile Gly His Arg Gly Ile Arg
660                 665                 670                 675

CTT GGA ACT ACT AAT CCA GAA ATT TAT GAA ATG CAA ATT AGA GCA TTC      2120
Leu Gly Thr Thr Asn Pro Glu Ile Tyr Glu Met Gln Ile Arg Ala Phe
                680                 685                 690

TTA GAA GCT ACT CGT GAA GTT ATT AAG GAA GGA ATT AAC GAT CAT CGA      2168
Leu Glu Ala Thr Arg Glu Val Ile Lys Glu Gly Ile Asn Asp His Arg
            695                 700                 705

GAA ATT ATG ATT CCA AAT GTT ACA GAA GTT AAT GAA CTT ATT AAC TTA      2216
Glu Ile Met Ile Pro Asn Val Thr Glu Val Asn Glu Leu Ile Asn Leu
        710                 715                 720

AGA AAG AAT GTT CTT GAA CCA GTT CAT GAA GAA GTT GAA AAG AAA TAT      2264
Arg Lys Asn Val Leu Glu Pro Val His Glu Glu Val Glu Lys Lys Tyr
725                 730                 735

GGT ATT AAA GTA CCA TTC TCG TAT GGT ACT ATG GTT GAA TGT GTT AGA      2312
Gly Ile Lys Val Pro Phe Ser Tyr Gly Thr Met Val Glu Cys Val Arg
                745                 750                 755
740

GCA GCA TTA ACA GCT GAT AAG ATT GCT ACA GAA GCT TCA TTC TTC TCA      2360
Ala Ala Leu Thr Ala Asp Lys Ile Ala Thr Glu Ala Ser Phe Phe Ser
            760                 765                 770

TTC GGA ACT AAT GAT CTT ACA CAA GGA ACA TTC TCA TAC TCA CGT GAA      2408
Phe Gly Thr Asn Asp Leu Thr Gln Gly Thr Phe Ser Tyr Ser Arg Glu
        775                 780                 785

GAT TCA GAA AAC AAA TTC ATT CCA AAA TAT GTT GAA CTT AAG ATT CTT      2456
Asp Ser Glu Asn Lys Phe Ile Pro Lys Tyr Val Glu Leu Lys Ile Leu
790                 795                 800

CCA GCT AAT CCA TTT GAA ATT CTT GAT AGA CCA GGT GTT GGA GAA GTT      2504
Pro Ala Asn Pro Phe Glu Ile Leu Asp Arg Pro Gly Val Gly Glu Val
                810                 815
805

ATG AGA ATT GCT GTT ACT AAA GGA AGA CAA ACA AGA CCA GAA TTA CTT      2552
Met Arg Ile Ala Val Thr Lys Gly Arg Gln Thr Arg Pro Glu Leu Leu
820                 825                 830                 835

GTT GGT ATT TGT GGA GAA CAC GGA GGA GAA CCA TCA TCA ATT GAA TGG      2600
Val Gly Ile Cys Gly Glu His Gly Gly Glu Pro Ser Ser Ile Glu Trp
                840                 845                 850

TGC CAC ATG ATT GGA TTG AAC TAT GTT TCA TGT TCT TCA TAC AGA ATT      2648
Cys His Met Ile Gly Leu Asn Tyr Val Ser Cys Ser Ser Tyr Arg Ile
            855                 860                 865

CCA GTT GCT AGA ATT GCT GCT GCT CAA GCC CAA ATT AGA CAT CCA AGA      2696
Pro Val Ala Arg Ile Ala Ala Ala Gln Ala Gln Ile Arg His Pro Arg
        870                 875                 880

GAA AAT TAAATTAACT TTTTTGGTTT                                        2722
Glu Asn
    885
```

(2) INFORMATION FOR SEQ ID NO:8:

(i) SEQUENCE CHARACTERISTICS:
        (A) LENGTH: 885 amino acids

-continued (B) TYPE: amino acid
   (D) TOPOLOGY: linear (ii) MOLECULE TYPE: protein (xi) SEQUENCE DESCRIPTION: SEQ ID NO:8:

```
Met Gln Arg Val Tyr Ala Phe Glu Asp Gly Asp Gly Thr Asn Lys Lys
 1               5                  10                  15

Leu Leu Gly Gly Lys Gly Ala Gly Leu Cys Thr Met Thr Lys Ile Gly
                20                  25                  30

Leu Pro Val Pro Gln Gly Phe Val Ile Thr Thr Glu Met Cys Lys Gln
             35                  40                  45

Phe Ile Ala Asn Gly Asn Lys Met Pro Glu Gly Leu Met Glu Glu Val
         50                  55                  60

Lys Lys Glu Tyr Gln Leu Val Glu Lys Lys Ser Gly Lys Val Phe Gly
 65                  70                  75                  80

Gly Glu Glu Asn Pro Leu Leu Val Ser Val Arg Ser Gly Ala Ala Met
                 85                  90                  95

Ser Met Pro Gly Met Met Asp Thr Ile Leu Asn Leu Gly Leu Asn Asp
                100                 105                 110

Lys Thr Val Val Ala Leu Ala Lys Leu Thr Asn Asn Glu Arg Phe Ala
            115                 120                 125

Tyr Asp Ser Tyr Arg Arg Phe Val Ser Leu Phe Gly Lys Ile Ala Leu
        130                 135                 140

Asn Ala Cys Asp Glu Val Tyr Asp Lys Thr Leu Glu Asn Lys Lys Val
145                 150                 155                 160

Glu Lys Gly Val Lys Leu Asp Thr Glu Leu Asp Ala Asn Asp Met Lys
                165                 170                 175

Glu Leu Ala Gln Val Phe Ile Lys Lys Thr Glu Glu Phe Thr Lys Gln
                180                 185                 190

Pro Phe Pro Val Asp Pro Tyr Ala Gln Leu Glu Phe Ala Ile Cys Ala
            195                 200                 205

Val Phe Arg Ser Trp Met Gly Lys Arg Ala Val Asp Tyr Arg Arg Glu
        210                 215                 220

Phe Lys Ile Thr Pro Glu Gln Ala Asp Gly Thr Ala Val Ser Val Val
225                 230                 235                 240

Ser Met Val Tyr Gly Asn Met Gly Asn Asp Ser Ala Thr Gly Val Cys
                245                 250                 255

Phe Thr Arg Asp Pro Gly Thr Gly Glu Asn Met Phe Phe Gly Glu Tyr
            260                 265                 270

Leu Lys Asn Ala Gln Gly Glu Asp Val Val Ala Gly Ile Arg Thr Pro
        275                 280                 285

Gln Ile Ile Ser Lys Met Ala Glu Asp Arg Asp Leu Pro Gly Cys Tyr
    290                 295                 300

Glu Gln Leu Leu Asp Ile Arg Lys Lys Leu Glu Gly Tyr Phe His Glu
305                 310                 315                 320

Val Gln Asp Phe Glu Phe Thr Ile Glu Arg Lys Lys Leu Tyr Met Leu
                325                 330                 335

Gln Thr Arg Asn Gly Lys Met Asn Ala Thr Ala Thr Val Arg Thr Gly
            340                 345                 350

Val Asp Met Val Glu Glu Gly Leu Ile Thr Lys Glu Gln Ala Ile Met
        355                 360                 365

Arg Ile Ala Pro Gln Ser Val Asp Gln Leu Leu His Lys Asn Met Pro
    370                 375                 380

Ala Asn Tyr Ala Glu Ala Pro Leu Val Lys Gly Leu Pro Ala Ser Pro
```

-continued

```
385                 390                 395                 400
Gly Ala Ala Thr Gly Ala Val Val Phe Asp Ala Asp Ala Val Glu
                405                 410                 415
Gln Ala Lys Gly Lys Lys Val Leu Leu Leu Arg Glu Glu Thr Lys Pro
                420                 425                 430
Glu Asp Ile His Gly Phe Phe Val Ala Glu Gly Ile Leu Thr Cys Arg
                435                 440                 445
Gly Gly Lys Thr Ser His Ala Ala Val Val Ala Arg Gly Met Gly Lys
                450                 455                 460
Pro Cys Val Ser Gly Ala Glu Gly Ile Lys Val Asp Val Ala Lys Lys
465                 470                 475                 480
Ile Ala Lys Ile Gly Ser Leu Glu Val His Glu Gly Asp Ile Leu Thr
                485                 490                 495
Ile Asp Gly Ser Thr Gly Cys Val Tyr Lys Gly Glu Val Pro Leu Glu
                500                 505                 510
Glu Pro Gln Val Gly Ser Gly Tyr Phe Gly Thr Ile Leu Lys Trp Ala
                515                 520                 525
Asn Glu Ile Lys Lys Ile Gly Val Phe Ala Ala Gly Asp Leu Pro Ser
                530                 535                 540
Ala Ala Lys Lys Ala Leu Glu Phe Gly Ala Glu Gly Ile Gly Leu Cys
545                 550                 555                 560
Arg Thr Glu Arg Met Phe Asn Ala Val Glu Arg Leu Pro Ile Val Val
                565                 570                 575
Lys Met Ile Leu Ser Asn Thr Leu Glu Glu Arg Lys Lys Tyr Leu Asn
                580                 585                 590
Glu Leu Met Pro Leu Gln Lys Gln Asp Phe Ile Gly Leu Leu Lys Thr
                595                 600                 605
Met Asn Gly Leu Pro Val Thr Val Arg Leu Leu Asp Pro Pro Leu His
                610                 615                 620
Glu Phe Leu Pro Thr Leu Glu Glu Leu Met Arg Glu Ile Phe Glu Met
625                 630                 635                 640
Lys Leu Ser Gly Lys Thr Glu Gly Leu Ala Glu Lys Glu Val Val Leu
                645                 650                 655
Lys Lys Val Lys Glu Leu Met Glu Val Asn Pro Met Ile Gly His Arg
                660                 665                 670
Gly Ile Arg Leu Gly Thr Thr Asn Pro Glu Ile Tyr Glu Met Gln Ile
                675                 680                 685
Arg Ala Phe Leu Glu Ala Thr Arg Glu Val Ile Lys Gly Ile Asn
                690                 695                 700
Asp His Arg Glu Ile Met Ile Pro Asn Val Thr Glu Val Asn Glu Leu
705                 710                 715                 720
Ile Asn Leu Arg Lys Asn Val Leu Glu Pro Val His Glu Glu Val Glu
                725                 730                 735
Lys Lys Tyr Gly Ile Lys Val Pro Phe Ser Tyr Gly Thr Met Val Glu
                740                 745                 750
Cys Val Arg Ala Ala Leu Thr Ala Asp Lys Ile Ala Thr Glu Ala Ser
                755                 760                 765
Phe Phe Ser Phe Gly Thr Asn Asp Leu Thr Gln Gly Thr Phe Ser Tyr
770                 775                 780
Ser Arg Glu Asp Ser Glu Asn Lys Phe Ile Pro Lys Tyr Val Glu Leu
785                 790                 795                 800
Lys Ile Leu Pro Ala Asn Pro Phe Glu Ile Leu Asp Arg Pro Gly Val
                805                 810                 815
```

```
Gly Glu Val Met Arg Ile Ala Val Thr Lys Gly Arg Gln Thr Arg Pro
            820                 825                 830

Glu Leu Leu Val Gly Ile Cys Gly Glu His Gly Gly Glu Pro Ser Ser
            835                 840                 845

Ile Glu Trp Cys His Met Ile Gly Leu Asn Tyr Val Ser Cys Ser Ser
850                 855                 860

Tyr Arg Ile Pro Val Ala Arg Ile Ala Ala Gln Ala Gln Ile Arg
865                 870                 875                 880

His Pro Arg Glu Asn
            885
```

(2) INFORMATION FOR SEQ ID NO:9:

(i) SEQUENCE CHARACTERISTICS:
        (A) LENGTH: 3180 base pairs
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: CDS
        (B) LOCATION: 142..3006

(xi) SEQUENCE DESCRIPTION: SEQ ID NO:9:

```
CTGAAATTCC CGTAATCTAT CATCATTTAC ACCACAAATC GATTCACATC CTCACCGAAT      60

AGAAATCAAA TATCATTTAC TCCATCTCAC GATCTCCTTT TGCTATTGCT GATACCTCAA     120

TTTCGCAGGT GAAGGCGGAC G ATG AGT TCG TTG TTT GTT GAA GGT ATG CCT       171
                       Met Ser Ser Leu Phe Val Glu Gly Met Pro
                                    5                   10

CTG AAG TCA GCC AAT GAG TCG TGC TTA CCG GCG AGC GTG AAG CAA CGG       219
Leu Lys Ser Ala Asn Glu Ser Cys Leu Pro Ala Ser Val Lys Gln Arg
        15                  20                  25

CGA ACC GGT GAT CTC AGG CGA TTG AAC CAC CAC CGT CAA CCG GCG TTT       267
Arg Thr Gly Asp Leu Arg Arg Leu Asn His His Arg Gln Pro Ala Phe
            30                  35                  40

GTC CGG GGG ATT TGC CGT CGG AAG TTG AGT GGA GTT AGC AGA ATA GAG       315
Val Arg Gly Ile Cys Arg Arg Lys Leu Ser Gly Val Ser Arg Ile Glu
45                  50                  55

TTG CGC ACC GGT GGT TTA ACT CTG CCA CGA GCG GTG CTT AAT CCG GTG       363
Leu Arg Thr Gly Gly Leu Thr Leu Pro Arg Ala Val Leu Asn Pro Val
        60                  65                  70

TCT CCT CCG GTA ACG ACG ACT AAA AAG AGG GTT TTC ACT TTT GGT AAA       411
Ser Pro Pro Val Thr Thr Thr Lys Lys Arg Val Phe Thr Phe Gly Lys
75                  80                  85                  90

GGA AAC AGT GAA GGC AAC AAG GAC ATG AAA TCC TTG TTG GGA GGA AAA       459
Gly Asn Ser Glu Gly Asn Lys Asp Met Lys Ser Leu Leu Gly Gly Lys
                95                  100                 105

GGT GCA AAT CTT GCA GAG ATG GCA AGC ATT GGC CTA TCA GTT CCT CCT       507
Gly Ala Asn Leu Ala Glu Met Ala Ser Ile Gly Leu Ser Val Pro Pro
            110                 115                 120

GGG CTC ACT ATT TCA ACT GAA GCA TGT GAG GAA TAT CAA CAA AAT GGA       555
Gly Leu Thr Ile Ser Thr Glu Ala Cys Glu Glu Tyr Gln Gln Asn Gly
            125                 130                 135

AAA AAA CTG CCT CCA GGT TTA TGG GAT GAG ATT CTG GAA GGC TTA CAG       603
Lys Lys Leu Pro Pro Gly Leu Trp Asp Glu Ile Leu Glu Gly Leu Gln
        140                 145                 150

TAT GTC CAG AAA GAG ATG TCT GCA TCT CTC GGT GAC CCG TCT AAA GCT       651
Tyr Val Gln Lys Glu Met Ser Ala Ser Leu Gly Asp Pro Ser Lys Ala
155                 160                 165                 170
```

```
CTC CTC CTT TCC GTC CGT TCG GGT GCT GCC ATA TCG ATG CCT GGT ATG      699
Leu Leu Leu Ser Val Arg Ser Gly Ala Ala Ile Ser Met Pro Gly Met
            175                 180                 185

ATG GAC ACT GTA TTG AAT CTC GGG CTT AAT GAT GAG GTC GTA GAT GGT      747
Met Asp Thr Val Leu Asn Leu Gly Leu Asn Asp Glu Val Val Asp Gly
            190                 195                 200

CTA GCT GCC AAA AGT GGA GCT CGC TTT GCC TAT GAC TCG TAT AGG AGG      795
Leu Ala Ala Lys Ser Gly Ala Arg Phe Ala Tyr Asp Ser Tyr Arg Arg
            205                 210                 215

TTT CTA GAT ATG TTT GGC AAC GTT GTA ATG GGT ATC CCA CAT TCG TTA      843
Phe Leu Asp Met Phe Gly Asn Val Val Met Gly Ile Pro His Ser Leu
            220                 225                 230

TTT GAT GAA AAG TTA GAG CAG ATG AAA GCT GAA AAA GGG ATT CAT CTC      891
Phe Asp Glu Lys Leu Glu Gln Met Lys Ala Glu Lys Gly Ile His Leu
235                 240                 245                 250

GAC ACT GAT CTC ACT GCT GCT GAT CTT AAA GAT CTT GCT GAG CAA TAC      939
Asp Thr Asp Leu Thr Ala Ala Asp Leu Lys Asp Leu Ala Glu Gln Tyr
            255                 260                 265

AAG AAC GTG TAT GTG GAA GCA AAG GGC GAA AAG TTT CCC ACA GAT CCA      987
Lys Asn Val Tyr Val Glu Ala Lys Gly Glu Lys Phe Pro Thr Asp Pro
            270                 275                 280

AAG AAA CAG CTA GAG TTA GCA GTG AAT GCG GTT TTT GAT TCT TGG GAC     1035
Lys Lys Gln Leu Glu Leu Ala Val Asn Ala Val Phe Asp Ser Trp Asp
            285                 290                 295

AGC CCA AGG GCC AAT AAG TAC AGG AGT ATT AAC CAG ATA ACT GGG TTA     1083
Ser Pro Arg Ala Asn Lys Tyr Arg Ser Ile Asn Gln Ile Thr Gly Leu
            300                 305                 310

AAG GGG ACC GCG GTT AAC ATT CAA TGC ATG GTG TTT GGC AAC ATG GGG     1131
Lys Gly Thr Ala Val Asn Ile Gln Cys Met Val Phe Gly Asn Met Gly
315                 320                 325                 330

AAC ACT TCA GGA ACC GGT GTT CTT TTC ACT AGG AAC CCA AGC ACT GGT     1179
Asn Thr Ser Gly Thr Gly Val Leu Phe Thr Arg Asn Pro Ser Thr Gly
            335                 340                 345

GAG AAG AAG CTG TAT GGG GAG TTT TTA GTC AAT GCT CAG GGA GAG GAT     1227
Glu Lys Lys Leu Tyr Gly Glu Phe Leu Val Asn Ala Gln Gly Glu Asp
            350                 355                 360

GTT GTT GCT GGG ATC AGA ACA CCA GAA GAT TTG GTG ACC ATG GAG ACT     1275
Val Val Ala Gly Ile Arg Thr Pro Glu Asp Leu Val Thr Met Glu Thr
            365                 370                 375

TGC ATG CCT GAA GCA TAC AGA GAG CTT GTG GAG AAC TGT GTG ATT TTA     1323
Cys Met Pro Glu Ala Tyr Arg Glu Leu Val Glu Asn Cys Val Ile Leu
380                 385                 390

GAG AGA CAC TAC AAA GAT ATG ATG GAT ATT GAA TTC ACA GTT CAA GAA     1371
Glu Arg His Tyr Lys Asp Met Met Asp Ile Glu Phe Thr Val Gln Glu
395                 400                 405                 410

AAC AGA CTT TGG ATG CTG CAA TGC CGA ACA GGG AAA CGT ACT GGG AAA     1419
Asn Arg Leu Trp Met Leu Gln Cys Arg Thr Gly Lys Arg Thr Gly Lys
            415                 420                 425

GGT GCG GTG AGA ATT GCA GTA GAT ATG GTG AAC GAA GGG CTA ATT GAT     1467
Gly Ala Val Arg Ile Ala Val Asp Met Val Asn Glu Gly Leu Ile Asp
            430                 435                 440

ACT AGA ACA GCA ATT AAG AGG GTT GAG ACT CAA CAT CTA GAT CAG CTT     1515
Thr Arg Thr Ala Ile Lys Arg Val Glu Thr Gln His Leu Asp Gln Leu
            445                 450                 455

CTT CAT CCA CAG TTT GAG AAT CCG TCT GCT TAC AAA AGC CAT GTG GTA     1563
Leu His Pro Gln Phe Glu Asn Pro Ser Ala Tyr Lys Ser His Val Val
            460                 465                 470

GCA ACC GGT TTG CCA GCA TCC CCT GGG GCA GCC GTG GGG CAG GTT GTG     1611
Ala Thr Gly Leu Pro Ala Ser Pro Gly Ala Ala Val Gly Gln Val Val
475                 480                 485                 490
```

```
TTC AGC GCA GAG GAT GCT GAA ACA TGG CAT GCA CAA GGA AAG AGT GCT   1659
Phe Ser Ala Glu Asp Ala Glu Thr Trp His Ala Gln Gly Lys Ser Ala
            495                 500                 505

ATC TTG GTA AGG ACT GAA ACA AGC CCA GAA GAT GTT GGT GGT ATG CAT   1707
Ile Leu Val Arg Thr Glu Thr Ser Pro Glu Asp Val Gly Gly Met His
        510                 515                 520

GCA GCA GCT GGA ATC TTA ACC GCT AGA GGA GGA ATG ACA TCA CAT GCA   1755
Ala Ala Ala Gly Ile Leu Thr Ala Arg Gly Gly Met Thr Ser His Ala
            525                 530                 535

GCA GTG GTG GCT CGC GGA TGG GGC AAA TGT TGT GTT TCT GGT TGT GCT   1803
Ala Val Val Ala Arg Gly Trp Gly Lys Cys Cys Val Ser Gly Cys Ala
        540                 545                 550

GAT ATT CGT GTG AAC GAT GAT ATG AAG GTT TTT ACG ATA GGT GAC CGT   1851
Asp Ile Arg Val Asn Asp Asp Met Lys Val Phe Thr Ile Gly Asp Arg
555                 560                 565                 570

GTG ATT AAA GAA GGT GAC TGG CTT TCA CTT AAT GGT TCA ACT GGC GAA   1899
Val Ile Lys Glu Gly Asp Trp Leu Ser Leu Asn Gly Ser Thr Gly Glu
                575                 580                 585

GTC ATA TTG GGT AAA CAG CTA CTG GCT CCA CCT GCA ATG AGC AAT GAT   1947
Val Ile Leu Gly Lys Gln Leu Leu Ala Pro Pro Ala Met Ser Asn Asp
            590                 595                 600

TTA GAA ACA TTC ATG TCA TGG GCT GAT CAA GCA AGG CGT CTC AAG GTT   1995
Leu Glu Thr Phe Met Ser Trp Ala Asp Gln Ala Arg Arg Leu Lys Val
        605                 610                 615

ATG GCA AAT GCA GAC ACA CCT AAT GAT GCA TTA ACA GCC AGA AAC AAT   2043
Met Ala Asn Ala Asp Thr Pro Asn Asp Ala Leu Thr Ala Arg Asn Asn
    620                 625                 630

GGT GCA CAA GGG ATC GGA CTC TGT AGA ACT GAA CAT ATG TTT TTC GCT   2091
Gly Ala Gln Gly Ile Gly Leu Cys Arg Thr Glu His Met Phe Phe Ala
635                 640                 645                 650

TCT GAC GAG AGG ATC AAA GCT GTA AGA AAG ATG ATC ATG GCG GTC ACT   2139
Ser Asp Glu Arg Ile Lys Ala Val Arg Lys Met Ile Met Ala Val Thr
                655                 660                 665

CCA GAA CAA AGA AAA GCG GCT CTA GAC CTC TTA CTC CCA TAC CAA AGA   2187
Pro Glu Gln Arg Lys Ala Ala Leu Asp Leu Leu Leu Pro Tyr Gln Arg
            670                 675                 680

TCC GAT TTT GAG GGC ATT TTC CGA GCA ATG GAT GGA CTT CCT GTA ACA   2235
Ser Asp Phe Glu Gly Ile Phe Arg Ala Met Asp Gly Leu Pro Val Thr
        685                 690                 695

ATC CGC CTT CTA GAC CCT CCA CTT CAT GAG TTT CTA CCC GAA GGT GAT   2283
Ile Arg Leu Leu Asp Pro Pro Leu His Glu Phe Leu Pro Glu Gly Asp
    700                 705                 710

CTA GAA CAC ATA GTG AAT GAA CTT ACA GCG GAT ACA GGC ATG AGC AAA   2331
Leu Glu His Ile Val Asn Glu Leu Thr Ala Asp Thr Gly Met Ser Lys
715                 720                 725                 730

GAT GAA ATC TAT TCA AGA ATC GAA AAA TTA TCC GAA GTG AAC CCT ATG   2379
Asp Glu Ile Tyr Ser Arg Ile Glu Lys Leu Ser Glu Val Asn Pro Met
                735                 740                 745

CTT GGT TTC CGT GGT TGC CGA TTA GGG ATT TCA TAC CCC GAG CTA ACA   2427
Leu Gly Phe Arg Gly Cys Arg Leu Gly Ile Ser Tyr Pro Glu Leu Thr
            750                 755                 760

GAA ATG CAA GTT CGT GCG ATC TTT CAA GCT GCA GTG TCT ATG AAC AAT   2475
Glu Met Gln Val Arg Ala Ile Phe Gln Ala Ala Val Ser Met Asn Asn
        765                 770                 775

CAG GGG GTG ACT GTA ATA CCA GAG ATC ATG GTT CCG TTA GTC GGA ACA   2523
Gln Gly Val Thr Val Ile Pro Glu Ile Met Val Pro Leu Val Gly Thr
    780                 785                 790

CCT CAG GAA TTA CGG CAT CAA ATC GGC GTA ATT CGT GGT GTA GCT GCA   2571
Pro Gln Glu Leu Arg His Gln Ile Gly Val Ile Arg Gly Val Ala Ala
795                 800                 805                 810
```

```
AAT GTT TTT GCT GAA ATG GGG CTG ACG TTG GAG TAT AAA GTG GGA ACG       2619
Asn Val Phe Ala Glu Met Gly Leu Thr Leu Glu Tyr Lys Val Gly Thr
                815                 820                 825

ATG ATT GAG ATT CCT CGA GCT GCT TTG ATT GCT GAT GAG ATT GCA AAA       2667
Met Ile Glu Ile Pro Arg Ala Ala Leu Ile Ala Asp Glu Ile Ala Lys
            830                 835                 840

GAA GCC GAG TTC TTT TCG TTT GGA ACC AAT GAT TTG ACC CAG ATG ACA       2715
Glu Ala Glu Phe Phe Ser Phe Gly Thr Asn Asp Leu Thr Gln Met Thr
            845                 850                 855

TTT GGG TAC AGC AGA GAT GAT GTT GGC AAG TTT TTG CCG ATT TAT CTT       2763
Phe Gly Tyr Ser Arg Asp Asp Val Gly Lys Phe Leu Pro Ile Tyr Leu
        860                 865                 870

TCT CAA GGC ATT CTG CAG CAT GAT CCA TTT GAG GTT CTT GAC CAG AAA       2811
Ser Gln Gly Ile Leu Gln His Asp Pro Phe Glu Val Leu Asp Gln Lys
875                 880                 885                 890

GGG GTG GGT CAA TTG ATC AAG ATG GCC ACG GAG AAA GGT CGT GCA GCC       2859
Gly Val Gly Gln Leu Ile Lys Met Ala Thr Glu Lys Gly Arg Ala Ala
                895                 900                 905

AAT CCT AAC TTA AAG GTT GGG ATA TGT GGG GAG CAT GGT GGA GAA CCT       2907
Asn Pro Asn Leu Lys Val Gly Ile Cys Gly Glu His Gly Gly Glu Pro
            910                 915                 920

TCT TCT GTT GCA TTT TTT GAC GGA GTT GGA CTA GAT TAT GTG TCG TGC       2955
Ser Ser Val Ala Phe Phe Asp Gly Val Gly Leu Asp Tyr Val Ser Cys
            925                 930                 935

TCT CCA TTC AGG GTT CCT ATC GCA AGG TTG GCC GCT GCA CAA GTC GTT       3003
Ser Pro Phe Arg Val Pro Ile Ala Arg Leu Ala Ala Ala Gln Val Val
        940                 945                 950

GTT TAAGCTTTGA AAGGAGGATG GCTTATTTGC TTCATGTTTT CCGCCATTGT            3056
Val
955

ATATTATTTT GGTTTCATCC TTATTGTAAT GGTGAAAATG AACGATGTTT AAACAAAACA     3116

ACCCATTATA TTTTGGTTTG GTATGCAATA ATCTACTTTT CAAACAAAAA AAAAAAAAA      3176

AAAA                                                                  3180

(2) INFORMATION FOR SEQ ID NO:10:

(i) SEQUENCE CHARACTERISTICS:
        (A) LENGTH: 955 amino acids
        (B) TYPE: amino acid
        (D) TOPOLOGY: linear (ii) MOLECULE TYPE: protein (xi) SEQUENCE DESCRIPTION: SEQ ID NO:10:

Met Ser Ser Leu Phe Val Glu Gly Met Pro Leu Lys Ser Ala Asn Glu
1               5                   10                  15

Ser Cys Leu Pro Ala Ser Val Lys Gln Arg Arg Thr Gly Asp Leu Arg
            20                  25                  30

Arg Leu Asn His His Arg Gln Pro Ala Phe Val Arg Gly Ile Cys Arg
        35                  40                  45

Arg Lys Leu Ser Gly Val Ser Arg Ile Glu Leu Arg Thr Gly Gly Leu
    50                  55                  60

Thr Leu Pro Arg Ala Val Leu Asn Pro Val Ser Pro Val Thr Thr
65                  70                  75                  80

Thr Lys Lys Arg Val Phe Thr Phe Gly Lys Gly Asn Ser Glu Gly Asn
                85                  90                  95

Lys Asp Met Lys Ser Leu Leu Gly Gly Lys Gly Ala Asn Leu Ala Glu
            100                 105                 110
```

-continued

```
Met Ala Ser Ile Gly Leu Ser Val Pro Pro Gly Leu Thr Ile Ser Thr
            115                 120                 125
Glu Ala Cys Glu Glu Tyr Gln Gln Asn Gly Lys Lys Leu Pro Pro Gly
130                 135                 140
Leu Trp Asp Glu Ile Leu Glu Gly Leu Gln Tyr Val Gln Lys Glu Met
145                 150                 155                 160
Ser Ala Ser Leu Gly Asp Pro Ser Lys Ala Leu Leu Leu Ser Val Arg
                165                 170                 175
Ser Gly Ala Ala Ile Ser Met Pro Gly Met Met Asp Thr Val Leu Asn
                180                 185                 190
Leu Gly Leu Asn Asp Glu Val Asp Gly Leu Ala Ala Lys Ser Gly
            195                 200                 205
Ala Arg Phe Ala Tyr Asp Ser Tyr Arg Arg Phe Leu Asp Met Phe Gly
210                 215                 220
Asn Val Val Met Gly Ile Pro His Ser Leu Phe Asp Glu Lys Leu Glu
225                 230                 235                 240
Gln Met Lys Ala Glu Lys Gly Ile His Leu Asp Thr Asp Leu Thr Ala
                245                 250                 255
Ala Asp Leu Lys Asp Leu Ala Glu Gln Tyr Lys Asn Val Tyr Val Glu
                260                 265                 270
Ala Lys Gly Glu Lys Phe Pro Thr Asp Pro Lys Lys Gln Leu Glu Leu
            275                 280                 285
Ala Val Asn Ala Val Phe Asp Ser Trp Asp Ser Pro Arg Ala Asn Lys
290                 295                 300
Tyr Arg Ser Ile Asn Gln Ile Thr Gly Leu Lys Gly Thr Ala Val Asn
305                 310                 315                 320
Ile Gln Cys Met Val Phe Gly Asn Met Gly Asn Thr Ser Gly Thr Gly
                325                 330                 335
Val Leu Phe Thr Arg Asn Pro Ser Thr Gly Glu Lys Lys Leu Tyr Gly
            340                 345                 350
Glu Phe Leu Val Asn Ala Gln Gly Glu Asp Val Val Ala Gly Ile Arg
            355                 360                 365
Thr Pro Glu Asp Leu Val Thr Met Glu Thr Cys Met Pro Glu Ala Tyr
            370                 375                 380
Arg Glu Leu Val Glu Asn Cys Val Ile Leu Glu Arg His Tyr Lys Asp
385                 390                 395                 400
Met Met Asp Ile Glu Phe Thr Val Gln Glu Asn Arg Leu Trp Met Leu
                405                 410                 415
Gln Cys Arg Thr Gly Lys Arg Thr Gly Lys Gly Ala Val Arg Ile Ala
            420                 425                 430
Val Asp Met Val Asn Glu Gly Leu Ile Asp Thr Arg Thr Ala Ile Lys
            435                 440                 445
Arg Val Glu Thr Gln His Leu Asp Gln Leu Leu His Pro Gln Phe Glu
450                 455                 460
Asn Pro Ser Ala Tyr Lys Ser His Val Val Ala Thr Gly Leu Pro Ala
465                 470                 475                 480
Ser Pro Gly Ala Ala Val Gly Gln Val Val Phe Ser Ala Glu Asp Ala
                485                 490                 495
Glu Thr Trp His Ala Gln Gly Lys Ser Ala Ile Leu Val Arg Thr Glu
            500                 505                 510
Thr Ser Pro Glu Asp Val Gly Gly Met His Ala Ala Gly Ile Leu
            515                 520                 525
Thr Ala Arg Gly Gly Met Thr Ser His Ala Ala Val Val Ala Arg Gly
530                 535                 540
```

-continued

```
Trp Gly Lys Cys Cys Val Ser Gly Cys Ala Asp Ile Arg Val Asn Asp
545                 550                 555                 560

Asp Met Lys Val Phe Thr Ile Gly Asp Arg Val Ile Lys Glu Gly Asp
                565                 570                 575

Trp Leu Ser Leu Asn Gly Ser Thr Gly Glu Val Ile Leu Gly Lys Gln
            580                 585                 590

Leu Leu Ala Pro Pro Ala Met Ser Asn Asp Leu Glu Thr Phe Met Ser
        595                 600                 605

Trp Ala Asp Gln Ala Arg Arg Leu Lys Val Met Ala Asn Ala Asp Thr
610                 615                 620

Pro Asn Asp Ala Leu Thr Ala Arg Asn Asn Gly Ala Gln Gly Ile Gly
625                 630                 635                 640

Leu Cys Arg Thr Glu His Met Phe Phe Ala Ser Asp Glu Arg Ile Lys
                645                 650                 655

Ala Val Arg Lys Met Ile Met Ala Val Thr Pro Glu Gln Arg Lys Ala
                660                 665                 670

Ala Leu Asp Leu Leu Leu Pro Tyr Gln Arg Ser Asp Phe Glu Gly Ile
            675                 680                 685

Phe Arg Ala Met Asp Gly Leu Pro Val Thr Ile Arg Leu Leu Asp Pro
690                 695                 700

Pro Leu His Glu Phe Leu Pro Glu Gly Asp Leu Glu His Ile Val Asn
705                 710                 715                 720

Glu Leu Thr Ala Asp Thr Gly Met Ser Lys Asp Glu Ile Tyr Ser Arg
                725                 730                 735

Ile Glu Lys Leu Ser Glu Val Asn Pro Met Leu Gly Phe Arg Gly Cys
                740                 745                 750

Arg Leu Gly Ile Ser Tyr Pro Glu Leu Thr Glu Met Gln Val Arg Ala
            755                 760                 765

Ile Phe Gln Ala Ala Val Ser Met Asn Asn Gln Gly Val Thr Val Ile
770                 775                 780

Pro Glu Ile Met Val Pro Leu Val Gly Thr Pro Gln Glu Leu Arg His
785                 790                 795                 800

Gln Ile Gly Val Ile Arg Gly Val Ala Ala Asn Val Phe Ala Glu Met
                805                 810                 815

Gly Leu Thr Leu Glu Tyr Lys Val Gly Thr Met Ile Glu Ile Pro Arg
            820                 825                 830

Ala Ala Leu Ile Ala Asp Glu Ile Ala Lys Glu Ala Glu Phe Phe Ser
835                 840                 845

Phe Gly Thr Asn Asp Leu Thr Gln Met Thr Phe Gly Tyr Ser Arg Asp
850                 855                 860

Asp Val Gly Lys Phe Leu Pro Ile Tyr Leu Ser Gln Gly Ile Leu Gln
865                 870                 875                 880

His Asp Pro Phe Glu Val Leu Asp Gln Lys Gly Val Gly Gln Leu Ile
                885                 890                 895

Lys Met Ala Thr Glu Lys Gly Arg Ala Ala Asn Pro Asn Leu Lys Val
            900                 905                 910

Gly Ile Cys Gly Glu His Gly Gly Glu Pro Ser Ser Val Ala Phe Phe
        915                 920                 925

Asp Gly Val Gly Leu Asp Tyr Val Ser Cys Ser Pro Phe Arg Val Pro
        930                 935                 940

Ile Ala Arg Leu Ala Ala Ala Gln Val Val Val
945                 950                 955
```

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:11:

GACGGCTAAA AAGAGGGT                                      18

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:12:

TATCGAGAAA CCTTCTATAC                                  20

(2) INFORMATION FOR SEQ ID NO:13:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:13:

GTTTTCCCAG TCACGAC                                      17

(2) INFORMATION FOR SEQ ID NO:14:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:14:

CAGGAAACAG CTATGAC                                      17

(2) INFORMATION FOR SEQ ID NO:15:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:15:

GATATCAATC CGGTGTCTCC TCC                              23

(2) INFORMATION FOR SEQ ID NO:16:

(i) SEQUENCE CHARACTERISTICS:
        (A) LENGTH: 34 base pairs
        (B) TYPE: nucleic acid

```
        (C) STRANDEDNESS: single
        (D) TOPOLOGY: linear (ii) MOLECULE TYPE: other nucleic acid (xi) SEQUENCE DESCRIPTION: SEQ ID NO:16:

CGGTGTCTCC TCCGGATATC ACGGCTAAAA AGAG                                    34

(2) INFORMATION FOR SEQ ID NO:17:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:17:

TTGATATCCC GGTTGTCTCC TCCGGTA                                            27

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:18:

GCAGAGATGA TGTTGGCAAG                                                    20

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:19:

CTTGCCAACA TCATCTCTGC                                                    20

(2) INFORMATION FOR SEQ ID NO:20:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:20:

CATATGCTCT GTCCGGCATA ATC                                                23

(2) INFORMATION FOR SEQ ID NO:21:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
```

(xi) SEQUENCE DESCRIPTION: SEQ ID NO:21:

CTCGAGGGAT CTCAATCATT G                                                  21

(2) INFORMATION FOR SEQ ID NO:22:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: other nucleic acid (xi) SEQUENCE DESCRIPTION: SEQ ID NO:22:

GCAATCTCTT CAGCAATC                                                      18

(2) INFORMATION FOR SEQ ID NO:23:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: other nucleic acid (xi) SEQUENCE DESCRIPTION: SEQ ID NO:23:

GCTTCTTTTC CAATCTCATC                                                    20

(2) INFORMATION FOR SEQ ID NO:24:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: other nucleic acid (xi) SEQUENCE DESCRIPTION: SEQ ID NO:24:

CGAAAAGAAA TCGGCTTC                                                      18

(2) INFORMATION FOR SEQ ID NO:25:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: other nucleic acid (xi) SEQUENCE DESCRIPTION: SEQ ID NO:25:

GAAAGATAAA TCTGCAAAAA CTTG                                               24

(2) INFORMATION FOR SEQ ID NO:26:

(i) SEQUENCE CHARACTERISTICS:
          (A) LENGTH: 19 base pairs
          (B) TYPE: nucleic acid
          (C) STRANDEDNESS: single
          (D) TOPOLOGY: linear (ii) MOLECULE TYPE: other nucleic acid (xi) SEQUENCE DESCRIPTION: SEQ ID NO:26:

GCCTTGAGCA AGATAAATC                                                     19

(2) INFORMATION FOR SEQ ID NO:27:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:27:

TTCTGGTCAA TAACCTCAAT G        21

(2) INFORMATION FOR SEQ ID NO:28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:28:

GCTTAAACAA TGACTTGTGC        20

(2) INFORMATION FOR SEQ ID NO:29:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:29:

CCAATCTCAT CAGCTATTAA AG        22

(2) INFORMATION FOR SEQ ID NO:30:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:30:

GCTTCTTTTG CAATCTCTTC        20

(2) INFORMATION FOR SEQ ID NO:31:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:31:

CGAAAAGAAC TCAGCTTC        18

(2) INFORMATION FOR SEQ ID NO:32:

(i) SEQUENCE CHARACTERISTICS:
        (A) LENGTH: 23 base pairs
        (B) TYPE: nucleic acid

```
        (C) STRANDEDNESS: single
        (D) TOPOLOGY: linear (ii) MOLECULE TYPE: other nucleic acid (xi) SEQUENCE DESCRIPTION: SEQ ID NO:32:

CAAGATAAAT CGGCAAAAAC TTG                                              23

(2) INFORMATION FOR SEQ ID NO:33:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:33:

GAATGCCTTG AGAAAGATAA ATC                                              23

(2) INFORMATION FOR SEQ ID NO:34:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:34:

CTTTCTGGTC AAGAACCTCA AATG                                             24

(2) INFORMATION FOR SEQ ID NO:35:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:35:

GCTTAAACAA CGACTTGTGC                                                  20

(2) INFORMATION FOR SEQ ID NO:36:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:36:

CTCACTGTTC GAAGAGAAGC                                                  20

(2) INFORMATION FOR SEQ ID NO:37:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
```

(xi) SEQUENCE DESCRIPTION: SEQ ID NO:37:

CATATGCTCT GTCCGGCATA ATC                                                                 23